(12) United States Patent
Reis et al.

(10) Patent No.: US 9,204,933 B2
(45) Date of Patent: *Dec. 8, 2015

(54) MODULAR INTERFACES AND DRIVE ACTUATION THROUGH BARRIER

(71) Applicant: Hansen Medical, Inc., Mountain View, CA (US)

(72) Inventors: Gene Reis, San Jose, CA (US); Gregory F. Hirth, Pleasanton, CA (US); Enrique Romo, Dublin, CA (US)

(73) Assignee: HANSEN MEDICAL, INC., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/075,255

(22) Filed: Nov. 8, 2013

(65) Prior Publication Data

US 2014/0069437 A1   Mar. 13, 2014

Related U.S. Application Data

(63) Continuation of application No. 12/352,551, filed on Jan. 12, 2009, now Pat. No. 8,602,031.

(51) Int. Cl.
*A61B 19/08* (2006.01)
*A61B 19/00* (2006.01)
*A61B 19/10* (2006.01)

(52) U.S. Cl.
CPC ............... *A61B 19/081* (2013.01); *A61B 19/10* (2013.01); *A61B 19/2203* (2013.01); *A61B 19/38* (2013.01); *A61B 2019/4868* (2013.01); *Y10T 74/19967* (2015.01)

(58) Field of Classification Search
USPC .................. 128/849–856; 600/121, 124–125; 606/1, 130, 144, 41; 700/245
See application file for complete search history.

(56) References Cited

U.S. PATENT DOCUMENTS

| | | | |
|---|---|---|---|
| 5,718,311 A * | 2/1998 | Victoria et al. | 192/3.28 |
| 8,206,406 B2 * | 6/2012 | Orban, III | 606/130 |
| 8,602,031 B2 * | 12/2013 | Reis et al. | 128/852 |

* cited by examiner

*Primary Examiner* — Ophelia A Hawthorne
(74) *Attorney, Agent, or Firm* — Dorsey & Whitney LLP; Scott M. Smith

(57) ABSTRACT

The invention relates generally to robotically controlled systems, such as medical robotic systems. In one variation, a robotic catheter system is configured with a sterile barrier capable for transmitting a rotary force from a drive system on one side of the barrier to surgical tool on the other side of the sterile barrier for performing minimally invasive diagnostic and therapeutic procedures. Modularized drive systems for robotics are also disclosed herein.

16 Claims, 26 Drawing Sheets

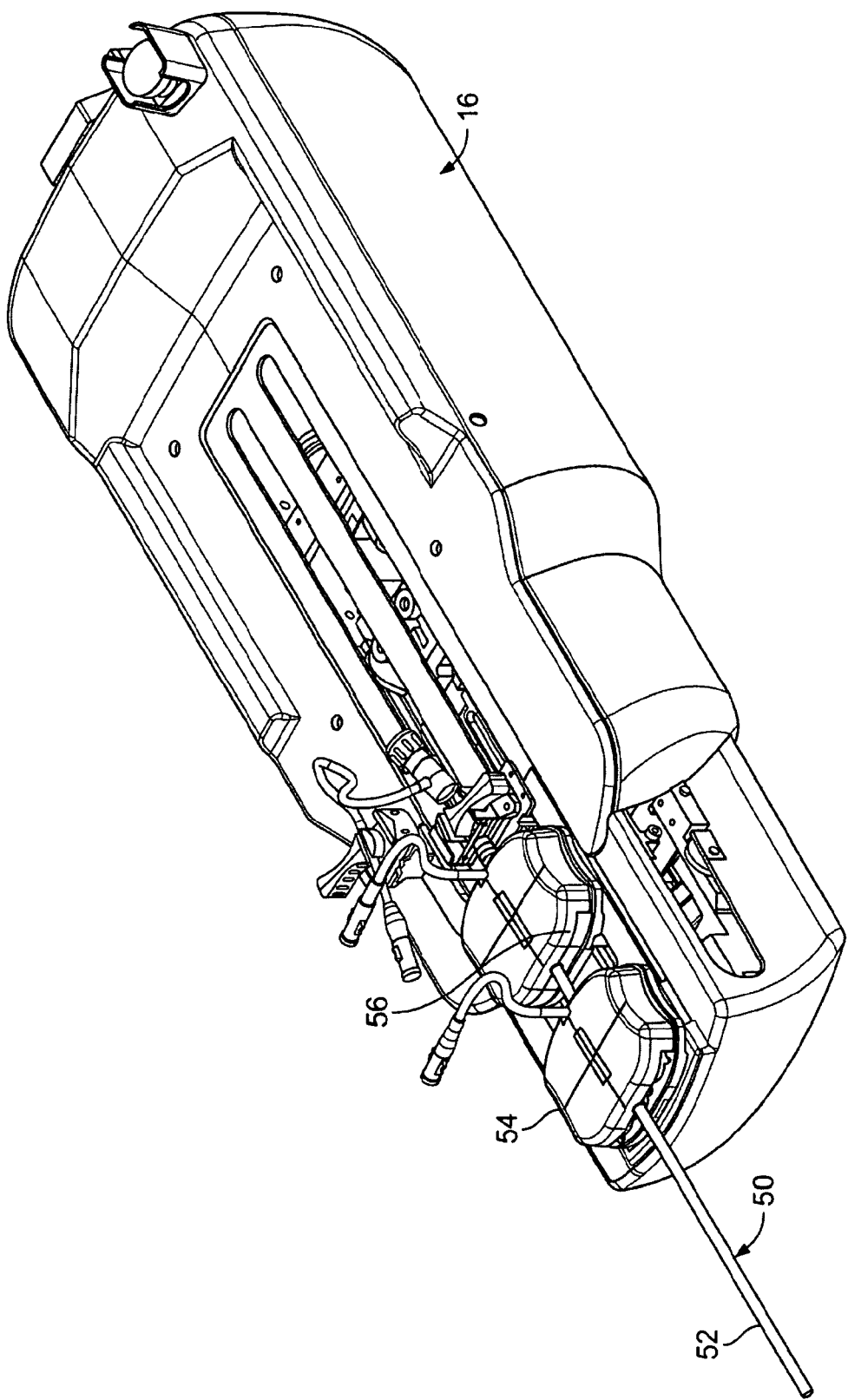

MODULAR INTERFACES AND DRIVE ACTUATION THROUGH BARRIER

CROSS-REFERENCE TO RELATED APPLICATIONS

This application is a continuation of U.S. patent application Ser. No. 12/352,551, filed on Jan. 12, 2009 and issued on Dec. 10, 2013 as U.S. Pat. No. 8,602,031, which is hereby expressly incorporated by reference in its entirety.

FIELD OF THE INVENTION

The invention relates generally to robotically controlled systems, such as medical robotic systems, and more particularly to a robotic system for performing minimally invasive diagnostic and therapeutic procedures.

BACKGROUND OF THE INVENTION

Robotic interventional systems and devices are well suited for use in performing various surgical, diagnostic or other medical procedures, as opposed to conventional techniques requiring a surgeon's hands to directly access internal organs. The benefits of robotic interventional systems are well known.

FIG. 1A illustrates an example of a robotic catheter manipulator ("RCM") 16 coupled to a medical tool 50. Typically, the medical tool 50 consists of a medical device 52 and one or more drive mechanisms 54 and 56. The drive mechanisms 54 and 56 allow a user controlling the RCM 16 to manipulate the medical device 52. Details on various drive systems are discussed below as well as in the commonly assigned patents and application referenced herein. In any case, the drive system or systems 54 (and/or 56) allow axial movement of the medical tool 50 along the RCM 16 as well as articulation of the medical device 52.

FIG. 1B illustrates the inner mechanisms of a conventional RCM 16. As shown, the motors 30 of the RCM 16 are affixed to the RCM 16 and convey rotation via a driver system 32 (including gears, belts, pulleys, and cables, and various other driver means to drive interface sockets 34 on the RCM 16. The interface socket 34 receives a portion of the drive mechanism of the tool engaged allowing motion to be transferred from the motors 32 ultimately to the medical tool 50. However, this configuration presents various challenges. In one example, rotation of the mechanism 54 about an axis of the RCM 16 requires a rotation of the motors 30 as well as the entire RCM 16. In addition, replacing a failed motor 30 requires significant servicing of the RCM 16 due to the complex interrelation of the various gears, belts, pulleys, and cables.

In addition, due to the complexity of the robotic system, it is difficult or impractical to attempt to sterilize the entire robotic assembly. Instead, the medical team establishes a sterile field over or adjacent to the robotic system. In one example, the sterile filed comprises the area above the drape, while the robotic side of the drape comprises a non-sterile environment. During such robotic procedures, it is common for the surgical team to place a sterile drape over the robotic assembly and then attach one or more sterilized tools onto the robotic assembly over through the drape.

The surgical tool must break the sterile barrier when it engages the non-sterile robotic assembly. This affects the ability of the surgical team to exchange surgical tools during a procedure. If the team wants to replace the surgical tool with a second tool, because of the tool's contacts with the non-sterile robotic assembly, the surgical tool is no longer sterile and cannot be re-installed. Clearly, this shortcoming hinders the surgical team when the use and reuse of surgical tools would be beneficial to an improved procedure.

One conventional method of overcoming this problem the addition of a sterile adaptor that is placed over the surgical drape. The sterile adaptor allows coupling of a surgical tool with the robotic assembly without breaking the sterile barrier. Currently used sterile adapters however have been complex assemblies that are costly and cumbersome.

There remains a need to provide a robotic assembly (or components for use in the robotic assembly) that allow for removal and replacement of surgical tools without breaking the sterile barrier while reducing the complexity of any sterile adaptor. There is also a need for a robotic system that offers simplified and modularized exchange of surgical tools while maintaining or even increasing the functionality of the robotic system by, for example, maintaining precision control of the surgical tool, preserving portability of the tool so that surgical team can replace various tools during a procedure, as well as increasing the ability of the tool to interact with the patient.

BRIEF SUMMARY OF THE INVENTION

Methods and devices described herein provide for improved coupling of medical tools to various medical systems. Such systems include robotic medical systems, medical driving tools, and other positioning systems.

A system according to the present disclosure can include modular drive systems (optionally for use with a robotic surgical system) comprising, at least one rotary drive mechanism, where a portion of the rotary drive mechanism comprises a wave generating cam (the cam may be a traditional cam or may include one or more moveable surfaces, or other features to assist in transfer of motion from the motor to the drive mechanism). The rotary drive mechanism can be coupled to a base that is removably coupleable to a robotic surgical system. The system can also include a sterilized medical tool comprising at least one gear drive (also known as a "splayer") used to actuate the tool. The gear drive typically engages at least one flexible spline gear (having a cup shape), where an interior of the cup shape removably engages the wave generating cam such that the wave generating cam deforms a portion of the cup. Continued rotation of the wave generating mechanism moves the deformed portion along the gear drive.

The rotary drive mechanism of the modular drive system can include a motor (or drive train output shaft) coupled to each wave generating cam. The wave generating cam can have any number of shapes consistent with a harmonic drive type of system. For example, the wave generating cam can include an elliptical shape. In additional variations, the wave generating cam comprises at least a first and a second rolling surface on each end, where each spherical surface engages the interior of the cup. Alternatively, the wave generator cam can include a ball/roller bearing or similar structure at a perimeter with a flexible outer face that remains stationary with respect to the flexible spline.

In addition, the drive mechanisms of the modular drive are adaptable to be moveable relative to an axis (axially moveable and/or rotatable) running along a length of the robotic surgical system.

The spline gear can include a plurality of spline teeth that engage a plurality of gear teeth of the gear drive. To effect driving of the system, the number of spline teeth is not equal to a number of gear teeth. The drape portion may comprise a different flexibility than the flexible spline cup. In most variations, the drape portion prevents direct contact between the sterilized medical tool and the remote control module to preserve sterility of the medical tool.

In another variation, the system and devices according to the present disclosure include a robotic manipulator comprising a drive system for comprising at least one wave generating cam coupled to a motor, where the drive assembly is affixed to a base; and a robotic control manipulator having at least one modular bay for removably docking the drive system, where the entire drive system is moveable relative to the robotic control manipulator.

One variation of the robotic manipulator can include a plurality of modular bays and further comprises a second drive system removably docked therein, where the second drive system is moveable relative to the robotic control manipulator. In an additional variation, robotic manipulator further includes a flexible spline cover located on the wave generating cam, a sterilized medical tool comprising at least one gear drive, the gear drive removeably located on the flexible spline cover, such that rotation of the wave generating cam causes a portion of the flexible spine cover to mesh with the gear drive to rotate the gear drive and actuate the medical tool.

In another variation, devices under the present disclosure include a surgical barrier for use with a medical positioning system having a medical tool, where the medical positioning system includes at least a rotary driver mechanism to affect a position of the medical tool and the medical tool includes a drive mechanism, the surgical barrier comprising: a sterilizable drape portion having a surgical side and a working side, where the working side is adapted to contact a portion of the medical positioning system preserving a sterile surgical field on the surgical side; at least one flexible cup in the drape portion and having a shape such that the working side of the cup receives a driver portion of the rotary driver mechanism and the surgical side of the cup nests within the drive mechanism of the medical tool; and where a surface of the surgical side of the cup is adapted to interact with the drive mechanism such a rotary motion of the driver portion within the cup section deforms the cup, where the surface of the surgical side of the cup drives the drive mechanism upon continued deformation of the cup.

In another variation, the device includes a flexible gear adapted to transfer motion from at least one rotary driver mechanism of a surgical system to a gear drive of a medical tool, the flexible gear comprising: at least one flexible spline cup having an interior working surface and a continuous exterior surgical surface where the flexible spline cup comprises a material capable of sterilization, the flexible spline cup having a shape such that the interior working surface of the flexible spline cup receives a driver of the rotary driver mechanism and the exterior surgical surface of the flexible spline cup nests within the gear drive, where rotary motion of the driver deforms, without rotating, the exterior surgical surface of the flexible spline cup such that continued deformation of the surgical surface engages the gear drive resulting in rotation of the gear drive; and a drape section extending from the flexible spline cup.

The invention also includes a method of driving a sterile medical tool with a non-sterile surgical system during a surgical procedure while maintaining a sterility of the surgical tool, the method comprising: placing a surgical drape over the surgical system where the drape comprises a working side to engage the surgical system and a sterile surgical side, the surgical drape including at least one flexible cup having a shape such that the working side of the cup receives a drive mechanism of the surgical system creating at least one deformed portion of the cup; coupling the sterile medical tool to the surgical system by placing at least one gear of the medical tool on the surgical side of the cup; and driving the medical tool by actuating the surgical system such that the drive mechanism of the surgical system causes movement of the at least one deformed portion of the flexible cup along the gear of the medical tool.

In one variation, the method further comprises removing the medical tool from the surgical drape while preserving a sterility of the medical tool. The medical tool can be subsequently re-coupled to the system without the need to re-sterilize. The method also includes coupling a second medical tool to the surgical system by placing at least one gear of the second medical tool on the surgical side of the cup.

In another variation, the surgical system comprises a portable surgical system and where the method further includes encapsulating or pouching the surgical system with the surgical drape.

Examples of medical systems that can be used with the methods devices and systems described herein are found in the following commonly assigned patent applications, each of which is incorporated by reference: U.S. 20060084945 Instrument Driver For Catheter Robotic System; 20080234631 Apparatus Systems and Methods for Flushing Gas from a Catheter of a Robotic Catheter System; and 20050222554 Robotic Catheter System.

The systems, devices and methods described herein are intended to illustrate the various aspects and embodiments of the invention. Where possible, the combination of various aspects as well as the combinations of various embodiments is intended to be within the scope of this disclosure.

BRIEF DESCRIPTION OF THE SEVERAL VIEWS OF THE DRAWINGS

The drawings illustrate the design and utility of illustrated embodiments of the invention, in which similar elements are referred to by common reference numerals, and in which:

FIG. 1A illustrates an example of a robotic catheter manipulator ("RCM").

FIG. 5C illustrates an exploded view of the circular spline gear as part of a drive pulley assembly that fits within a drive mechanism.

FIG. 5D shows one variation of a drive mechanism with four drive pulley assemblies.

DETAILED DESCRIPTION OF THE INVENTION

Methods, systems, and devices are described herein that improve on various drive systems that are used with complex medical systems. The drive systems described herein employ a harmonic gear drive configuration that permits a reduction in the size of the motors used to drive the tools as well as drive systems that allow for a medical practitioner to interchange various medical tools on the medical system without compromising a sterility of the tool.

Figure 1B:
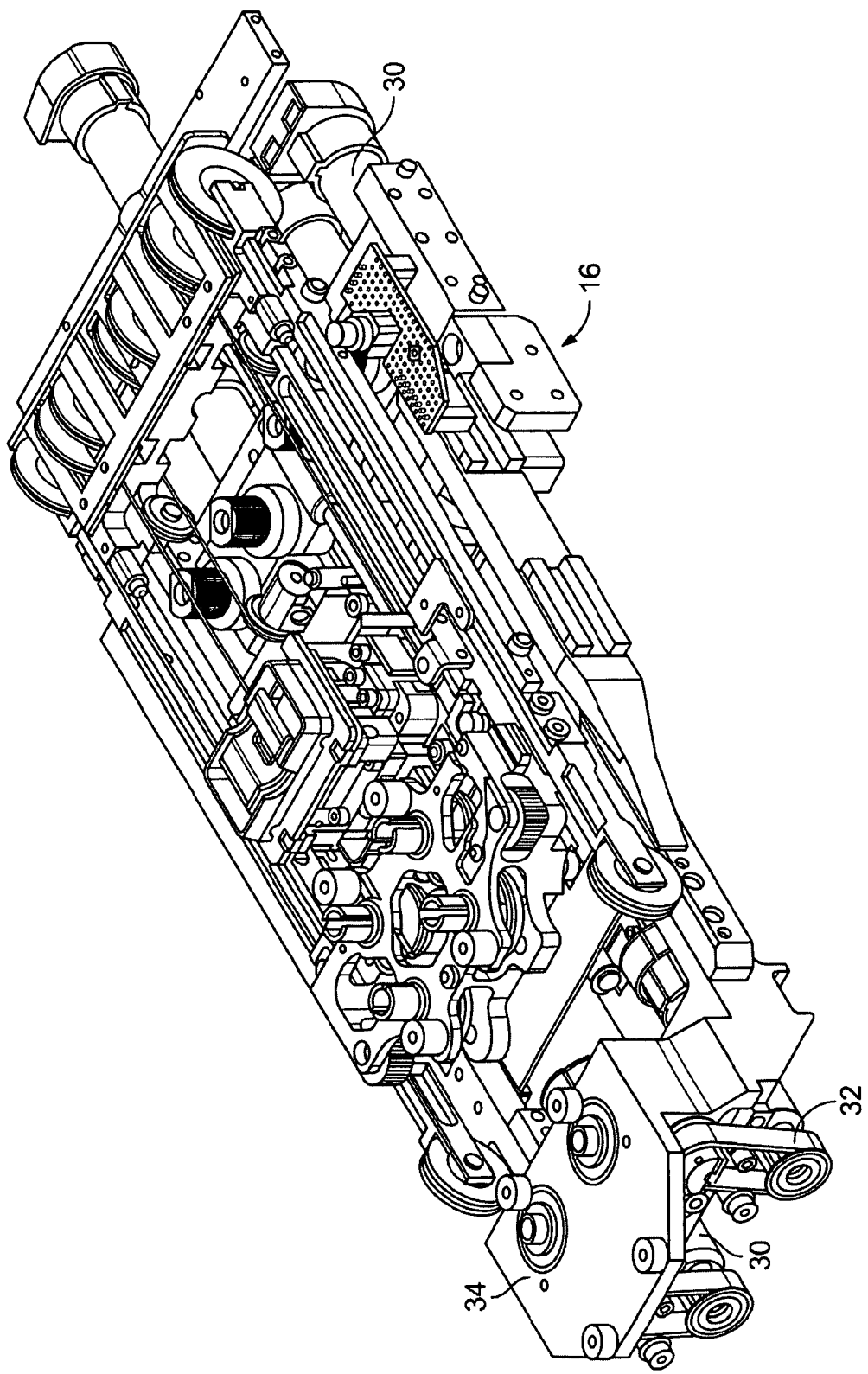
FIG. 1B illustrates the inner mechanisms of a conventional RCM.
Figure 2:
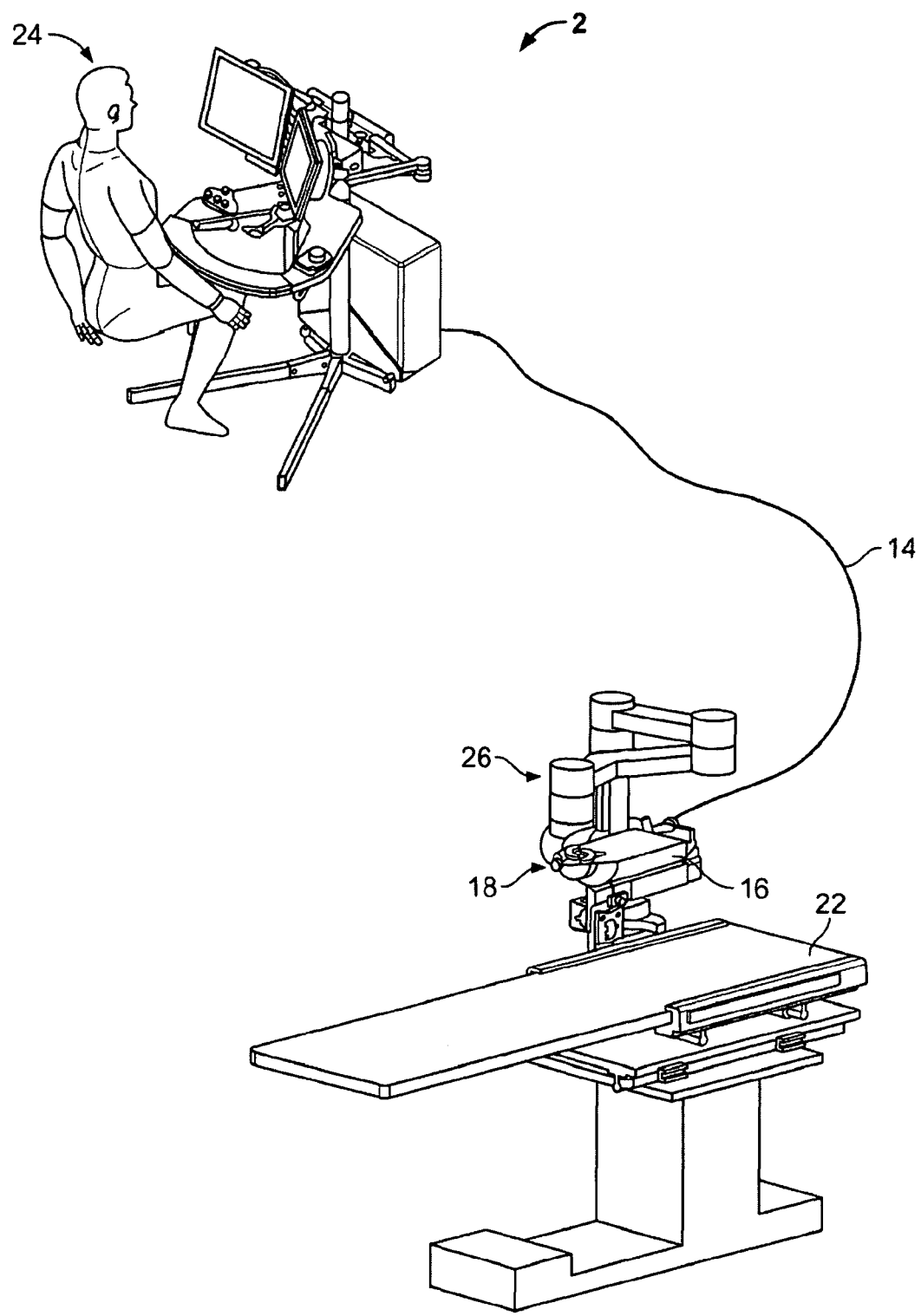
FIG. 2 illustrates one variation of a medical system using an RCM to manipulate a medical tool.

FIG. 2 illustrates one example of a medical system that benefits from the methods, devices and systems described herein. In this example, the system is a robotic catheter system 26. The system 26 can include an operator control station 2 located remotely from an operating table 22, to which a robotic catheter manipulator (RCM) 16 and instrument or medical tool 18 are coupled. A communication link 14 transfers signals between the operator control station 2 and RCM 16. It is noted, the medical systems within the scope of this disclosure can include stand alone systems that could be attached to a table 22 or other surgical equipment (in addition to the system illustrated in FIG. 2). Furthermore, variations of medical systems under this disclosure can include a single surgical motor or actuator that drives a medical tool where the surgical motor or actuator is a portable tool or is otherwise affixed to the surgical field.

Figure 3A:
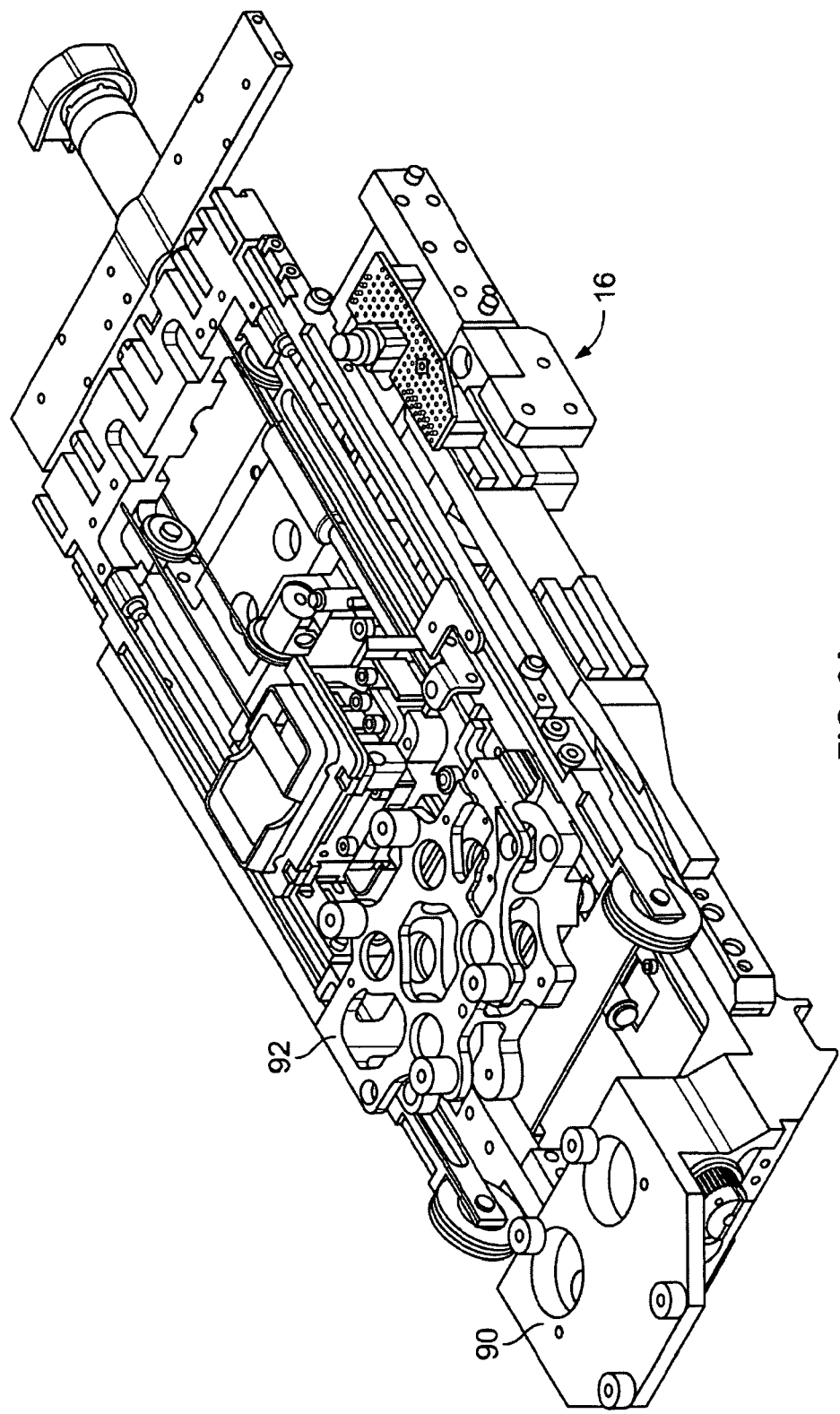
FIG. 3A illustrates a variation of an RCM adapted to accommodate a variety of tool/driver modules.
Figure 3B:
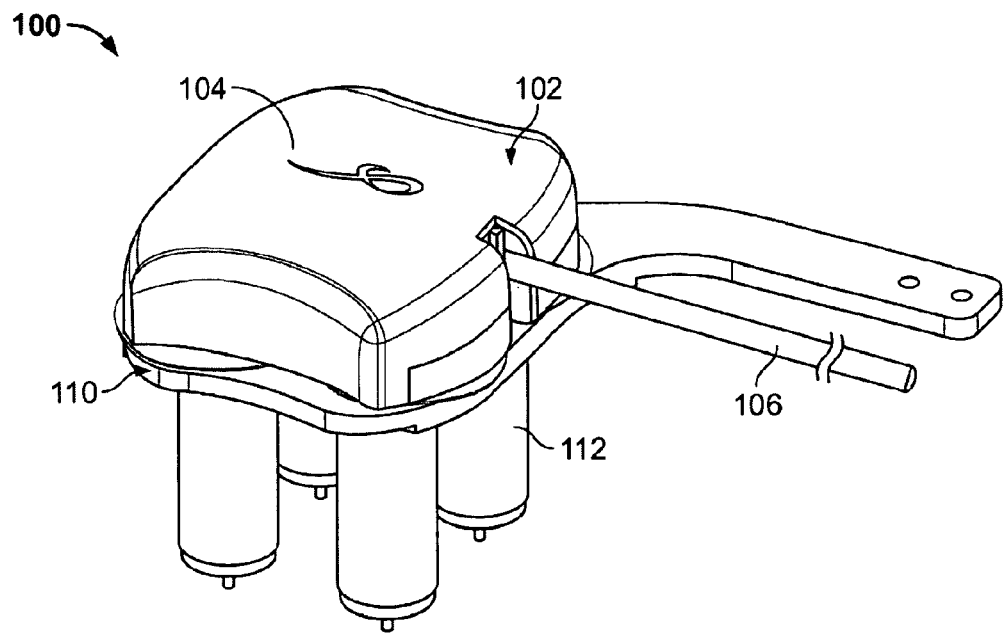
FIG. 3B shows one example of a modular tool/driver assembly.

FIG. 3A illustrates a variation of an RCM 16 adapted to accommodate a variety of tool/driver modules 100 (as shown in FIG. 3B). The interface module 100 includes a medical tool 102 comprising a drive mechanism 104 that manipulates a medical device 106.

The medical devices 106 within the scope of this disclosure can include any number of medical devices used for surgical procedures. For example, in some variations the medical device 106 is simply a steerable sheath or introducer used to deliver additional medical devices therethrough where the additional medical devices have a working end to perform a surgical, therapeutic, or diagnostic function. In additional variations, the medical device includes a steerable shaft or catheter that has a working end for performing the surgical, therapeutic, or diagnostic function.

While the illustration shows a single drive mechanisms 104 variations of the present disclosure can include one or more drive mechanisms depending on the number of devices 106 or the degrees of freedom required by the particular application.

The tool/driver module shown 100 also includes a driver system 110. As discussed below, the medical tool 102 is removably engageable with the driver system. The driver system 110 includes one or more motors 112 directly engageable with the drive mechanism 104 of the medical tool 102.

As shown in FIG. 3A, the RCM 16 is simplified since the motors, gear, belts, pulleys, cables, etc. that drive the medical tool are no longer part of the RCM 16. Accordingly, the RCM 16 includes open spots or bays 90 where the tool/driver modules 100 can be inserted. As noted below, RCM 16 under the present disclosure can include any number of bays 90 so that a number of medical tools 102 can be manipulated by the RCM 16. This feature along with the modular nature of the tool/driver modules 100 allow a medical practitioner to add or subtract capability to the system by installing or removing various tool/driver modules 100. In certain variations, the modules would be readily identifiable by the system's control unit 2 for immediate use. Such a "plug-n-play" effect increases the utility of such RCMs 16. Different tools or medical devices might require modules 100 with different characteristics, features, or interfaces. Accordingly, a medical practitioner can readily change or add a desired tool with minimal delay.

In addition, the modular nature of the RCM 16 and tool/driver module 100 allows ease of replacement of defective motors or other components. Such defective parts can be replaced. In contrast, systems in which the driver system is incorporated into the RCM will be inoperable during maintenance.

Figure 4A:
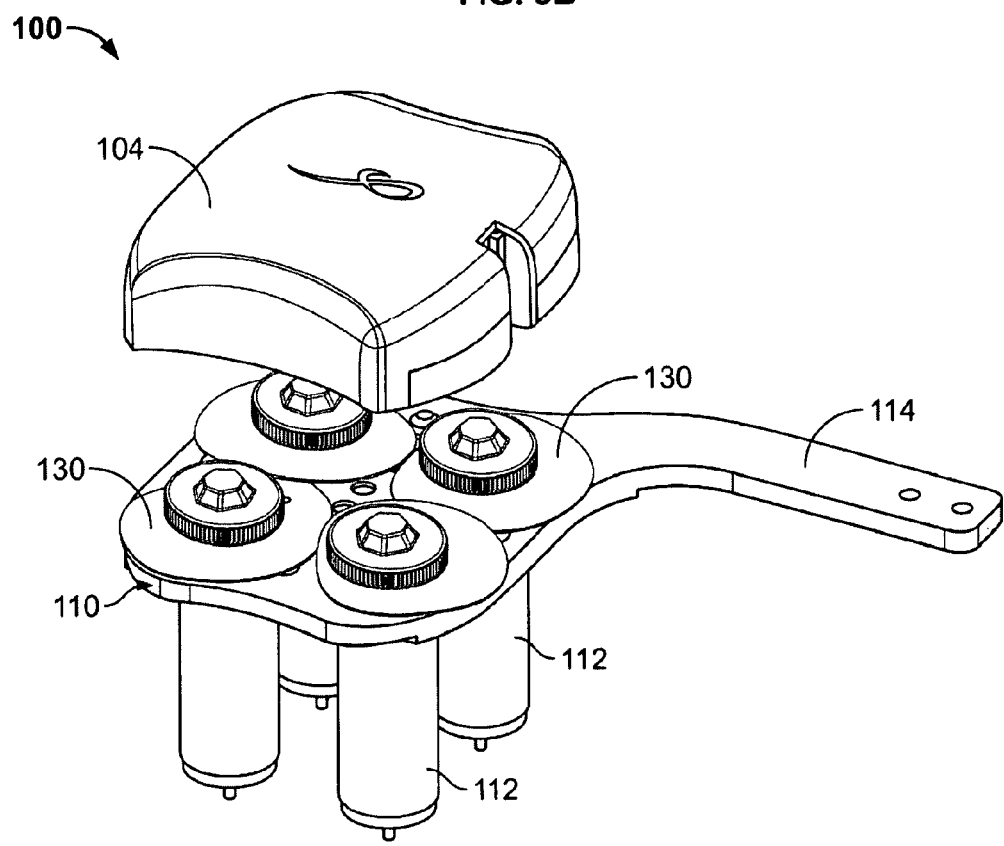
FIGS. 4A to 4C illustrate a variation of a tool/driver module with the drive mechanism removed from the driver system.
Figure 4B:
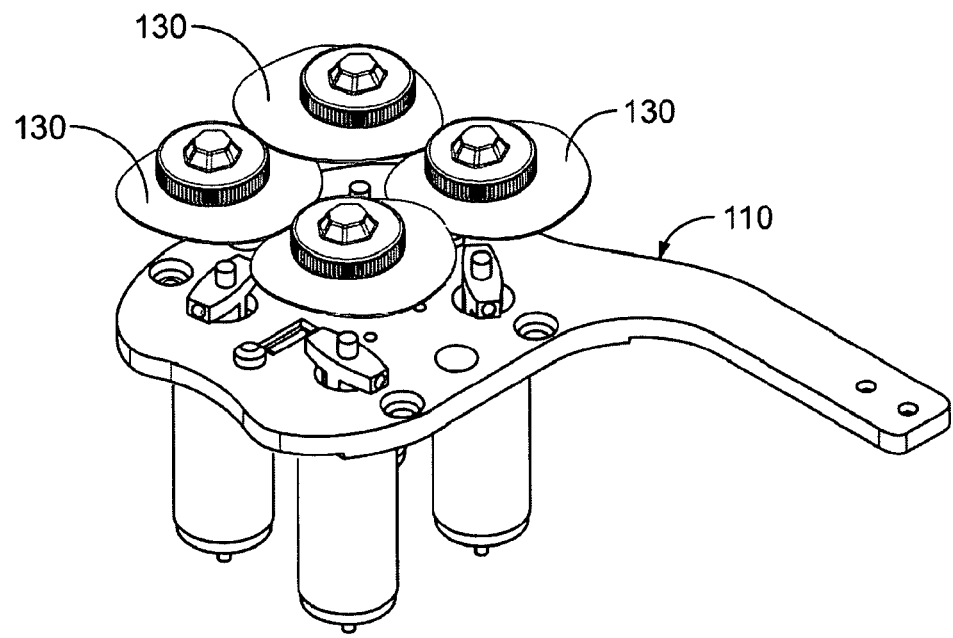
Figure 4C:
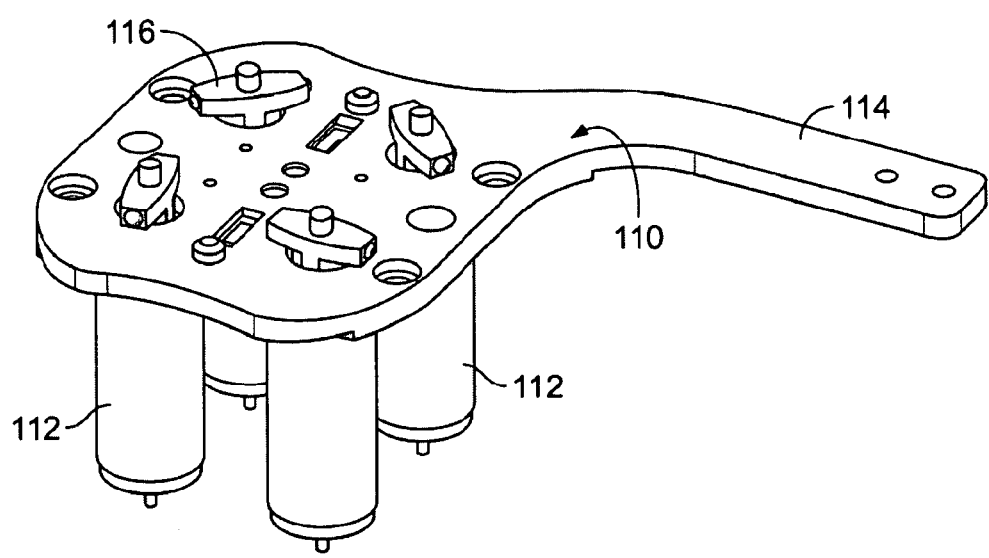

FIGS. 4A to 4C illustrate a variation of a tool/driver module 100 with the drive mechanism 104 removed from the driver system 110. As illustrated, the driver mechanism 110 includes any number of motors 112 coupled together via a baseplate 114. In certain variations, the baseplate 114 is secured within a bay 90 of the RCM 16. Alternatively, the motor could be directly secured within the RCM 16 without any baseplate. In addition, any cables/wiring/or other connectors that couple the motors 112 to the RCM 16 and control station 2 are omitted for purposes of clarity.

In operation, either the entire tool/driver module 100 can be inserted into a RCM 16. Alternatively, the tool 102 or drive mechanism 104 can be removed from the module 100 so that the driver system 110 alone is inserted into (or remains in) the bays of the RCM 16. In these latter variations, the tool/driver module 100 can include a flexible gear 130. While the flexible gear 130 can provide several functions, primarily, the flexible gear 130 serves as a component of a harmonic drive type system. The features of the flexible gear are discussed in detail below.

FIGS. 4B and 4C illustrates the flexible gear 130 being removed from the driver system 110. As shown, motors 112 are secured to a baseplate 114 so that a portion of the motor extends above the baseplate 114. In a harmonic drive type system, this portion comprises a wave generator or wave generating cam 116. The rotation of the wave generating cam 116 of the driver system 110 is transferred through the flexible gear 130 to the drive mechanism 104 to ultimately pre-position, bend, steer, or actuate the medical device (not shown).

Figure 5A:
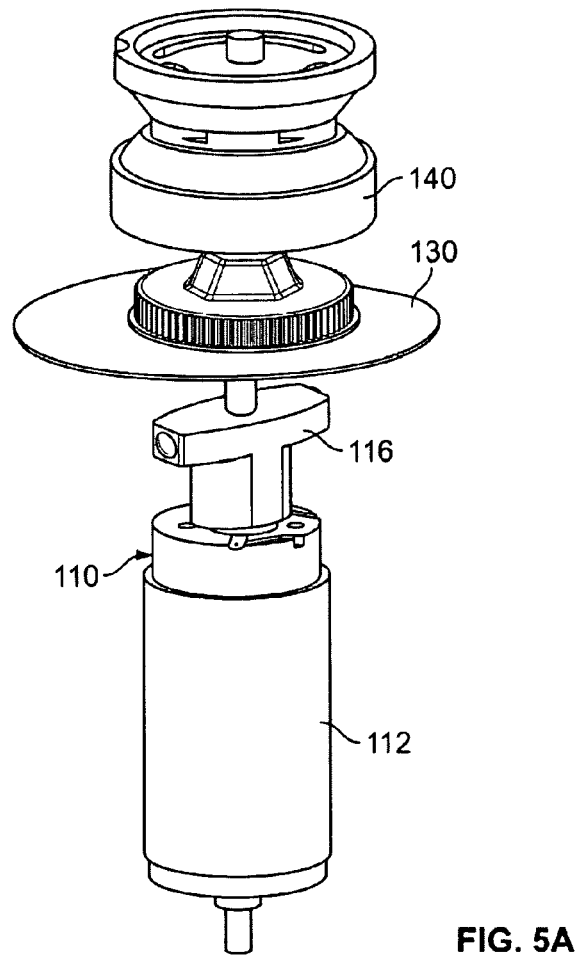
FIGS. 5A and 5B illustrate a variation of a harmonic drive configuration according to the principles described herein.
Figure 5B:
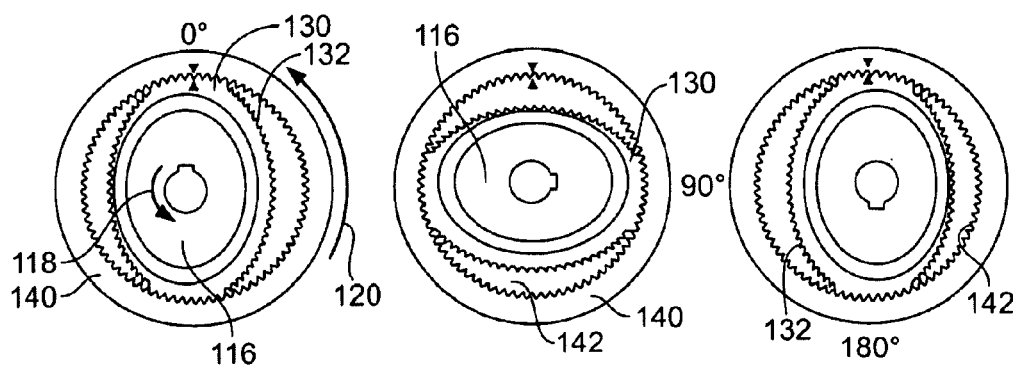
Figure 5C:
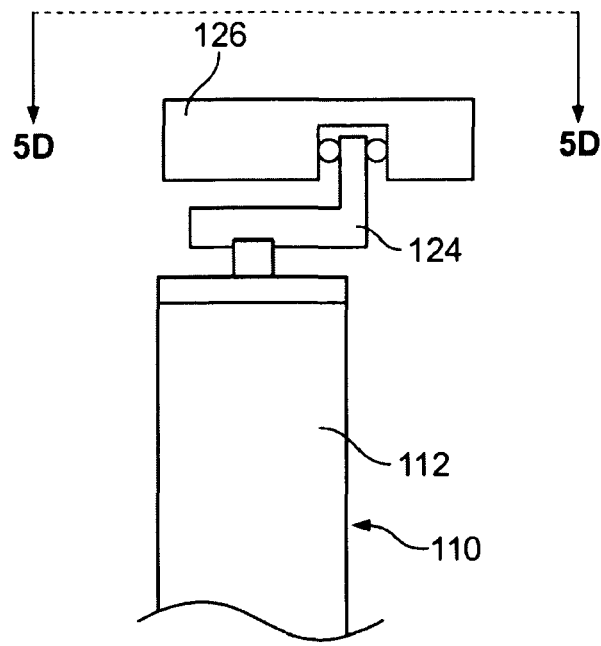
FIGS. 5C through 5F illustrate an additional variation of a drive system using a cam follower type driver.

FIGS. 5A and 5B illustrate a variation of a harmonic drive configuration for use with the present device and system. A typical harmonic drive mechanism consists of three components, a wave generator, a flex spline, and a circular spline. FIG. 5A illustrates a disassembled view of the motor 112 with a wave generator 116 attached. The wave generator or wave generating cam 116 nests within a flexible spline gear 130. Typically, the flexible spline gear comprises a shallow cup type structure with a rigid bottom and flexible sidewalls having a number of spline teeth 132 on the outer surface. The flexible spline gear 130 transfers rotation from the wave generating cam 116 to a circular spline or gear 140 that is part of the drive mechanism 104 of the medical tool. The circular gear 140 is typically a rigid ring with gear teeth 142 on its inner surface.

FIG. 5B shows a variation of the interaction between the wave generating cam 116 against the flexible spline gear 130 to drive the circular spline or gear 140. The elliptical nature of the wave generating cam 116 deforms the flexible spline gear 130 at opposing ends. In the illustrated variation, the ends of the wave generating cam 116 as well as the interior surface of the wave spline gear 130 are smooth. However, one or more of these surfaces can optionally include teeth or other features to assist in driving the system. The exterior surface of the flexible spline 130 includes a number of spline teeth 132. These spline teeth 132 engage an interior surface of the circular gear 140 that can have a number of gear teeth 142. When assembled, the flexible spline 130 mounts onto the wave generating cam 116 so that the wave generating cam 116 fits within the cup structure of the flexible spline 130. The circular gear 140 is then mounted onto the flexible spline 130 so that the spline teeth 132 on the outer surface of the flexible spline 130 mate with the gear teeth 142 on the inner surface of the circular gear or circular spline 140. The elliptical nature of the wave generating cam 116 deforms the flexible spline 130 to engage the circular spline 140 at two regions on opposite sides of the flexible spline 130. The wave generating cam 116 is then driven in a circular motion causing the deformed portion of the flexible spline 130 to move or orbit about its axis. Conventional harmonic configurations require either the flex spline or the circular spline to be constrained from rotating. This permits rotary motion of the wave generating cam 116 to transfer to the other non-rotating member. In one variation of the present configuration, the flex spline 130 does not rotate and is maintained in a stationary position. Thus, the movement of the wave generating cam 116 causes movement in the spline gear 140. The harmonic drive configuration provides a tool/driver module 100 with inherent gear reduction and zero backlash.

The number of spline teeth 132 on the flexible spline 130 is different from the number of gear teeth 142 on the circular spline gear 140. The difference in the number of spline teeth 132 and gear teeth 142 cause the circular gear 140 to rotate a slight amount for every full rotation of the wave generating cam 116.

As the motor 112 rotates the wave generating cam 116, the deformed portion of the flexible spline 130 moves in a wave-like motion causing meshing of the spline teeth 132 against the gear teeth 142 of the circular gear 140 at their two equidistant points of engagement. This meshing progresses in a continuous rolling fashion. It also allows for full tooth disengagement at the two points along the minor axis of the wave generator. Since the number of teeth are different, and because full tooth disengagement is made possible by the elliptical shape of the wave generator cam 116, each complete revolution of the wave generator cam 116 a displacement equal to the difference in the number of teeth, This displacement is always in the opposite direction of the rotation of the wave generating cam 116 as shown by arrows 118 and 120 in FIG. 5B. In one variation, the difference in the number of spline teeth 132 and gear teeth 142 is two (namely that there are two fewer spline teeth 132 than gear teeth 142.) However, additional configurations are within the scope of this disclosure.

Another benefit of the present configuration is that the tool/driver module 100 is intended to be disassembled and reassembled by the user during operation. As noted above, the flexible spline gear 130 itself can form a sterile barrier. Thus the driver system 110 and flex spline gear 130 can remain in place while the circular spline gear 140 is integrated into the drive mechanism 140 and can be replaced without comprising the sterile field of the surgical procedure.

Figure 5D:
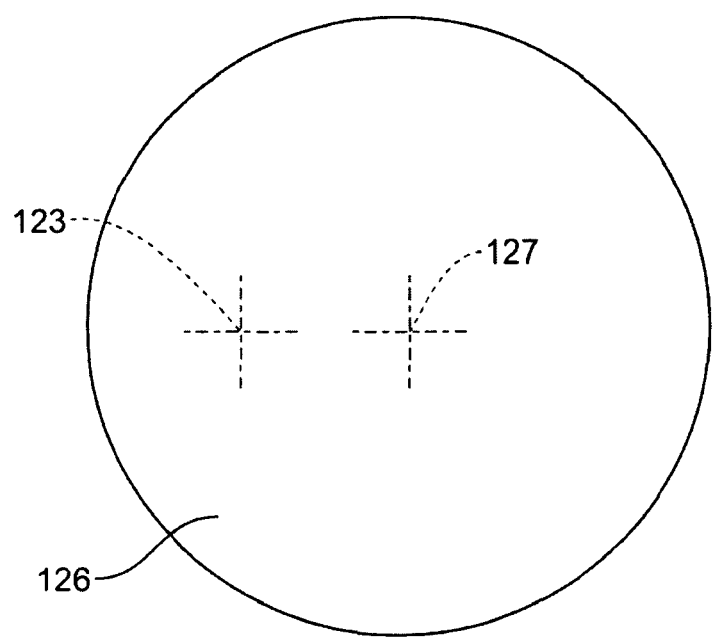
Figure 5E:
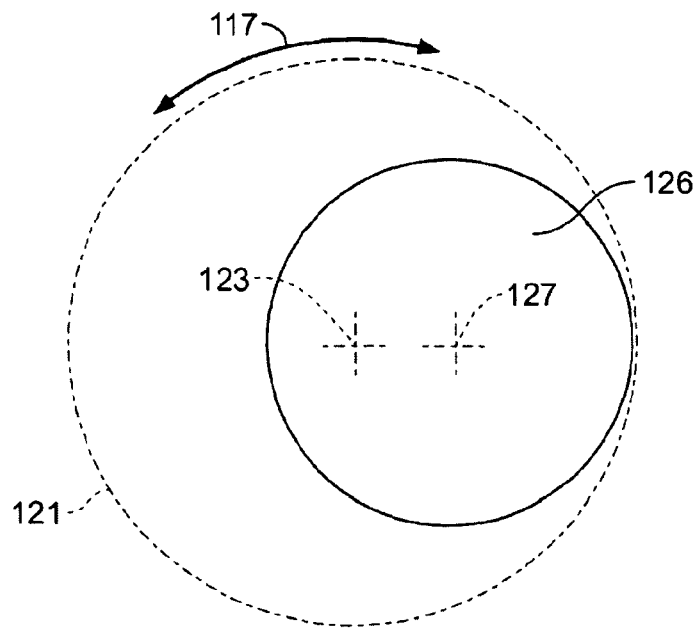

FIGS. 5C to 5F illustrate an alternate gear drive system 110. In this variation, a motor 112 is coupled to and rotates a camshaft 124 that drives a cam follower 126. FIG. 5D shows a top view of the cam follower 126 as seen from line 5D-5D in FIG. 5C. The center of the cam follower 127 can be offset from an axis or center of rotation of the motor 123. As shown in FIG. 5E, rotation of the motor 112 causes the cam shaft 124 to rotate and drive the cam follower 126 about the axis of the motor 123 rather than about the center of the cam follower 127. Accordingly, the cam follower 126 moves about an orbital path 121 in either direction 117 rather than only a rotational path about its own center 127. The camshaft 124 and cam follower 126 can include any number of bearings or bearing surface at the interface to allow the camshaft 124 to rotate independently of the cam follower 126. Alternatively, in an additional variation, the two parts could be affixed together.

Figure 5F:
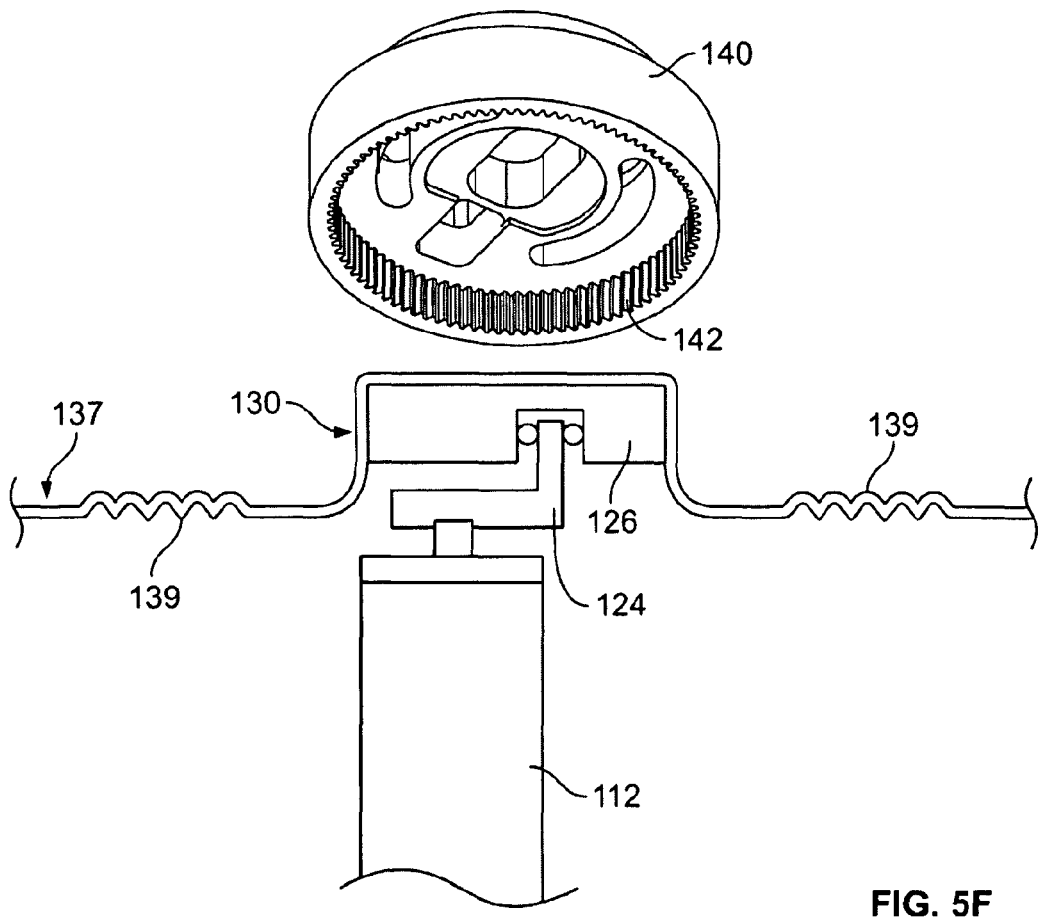

FIG. 5F shows a variation of a gear drive system 110 having a flexible spline 130 located over the cam follower 126. As discussed herein, the exterior of the flexible spline 130 includes a number of spine teeth (not shown) that engage a number of gear teeth 142 located on a circular spline gear 140. The orbital rotation 121 of the cam follower 126 moves the flexible spline 130 in an x-y direction (along the inner perimeter of the circular spline gear 140) so that it can engage the interior gear teeth 142 of the spline gear as the motor 112 drives the camshaft 124. As noted herein, the flexible spline 130 can include a barrier portion 137 having a flexure area 139 that accommodates movement of the flexible spline 130 in the x-y direction relative to the barrier portion 137. At the same time, the flexible spline 130, being affixed to the barrier 137 via the flexure area 139 does not rotate. The system 110 can be designed to select a rate of rotation of the spline gear 140 relative to the rotation of the flexible spline gear. The circular spline gear 140 will rotate relative to the rotation of the motor shaft 112 by a multiple of spline teeth/gear teeth. In other words, the circular spline gear 140 will rotate N times as much as the motor shaft where N=# of spline teeth/# of gear teeth.

Figure 6A:
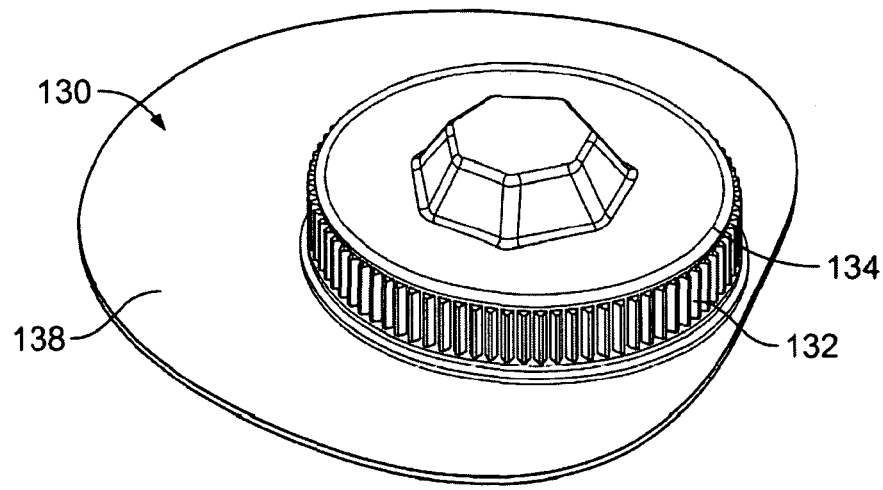
FIGS. 6A through 6D show one variation of a flexible spline cup.
Figure 6B:
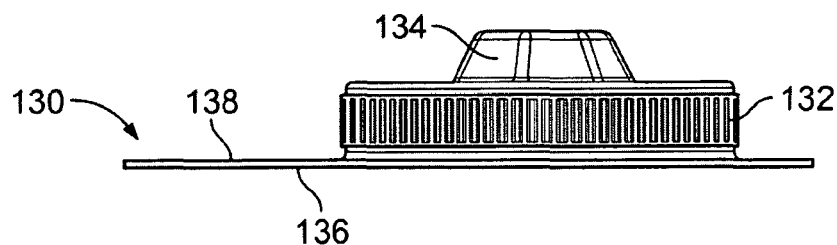
Figure 6C:
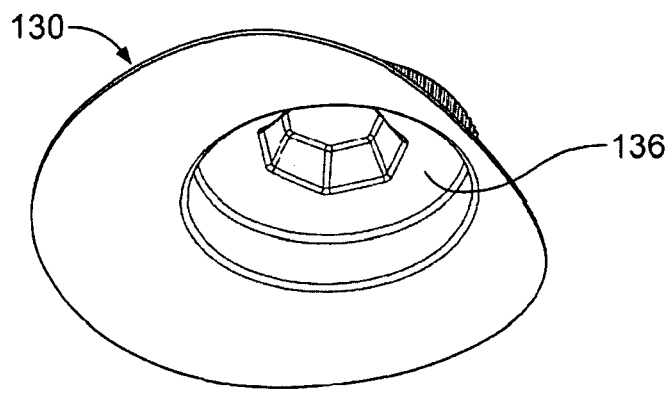

FIGS. 6A through 6D show one variation of a flexible spline gear 130. FIGS. 6A and 6B show perspective and side views of the spline gear 130 as having a cup section 134 with a number of spline teeth 132 on an outer surface of the flexible spline 130. Once sterilized, this outer surface forms a working surgical surface or surgical side that can enter the sterile filed of the operating room. Accordingly, the surgical side 138 can extend from the cup shape 134. In additional variations, the surgical surface 138 of a flexible spline gear 130 may not have teeth but can be formed into a surface that engages the circular spline for transmission of a rotational force. In addition, the cup shape 134 can be fabricated from a material that is flexible and can withstand an acceptable sterilization process (e.g., nylon, plastic, a flexible metal, etc.). FIG. 6C shows a bottom perspective view of a flexible spline gear 130. As discussed previously, the working side 136 of the spline gear 130 typically contacts a wave generator or other non-sterile environment. The working surface can comprise a smooth surface or can have varying textures to increase gripping of the wave generator cam.

Figure 6D:
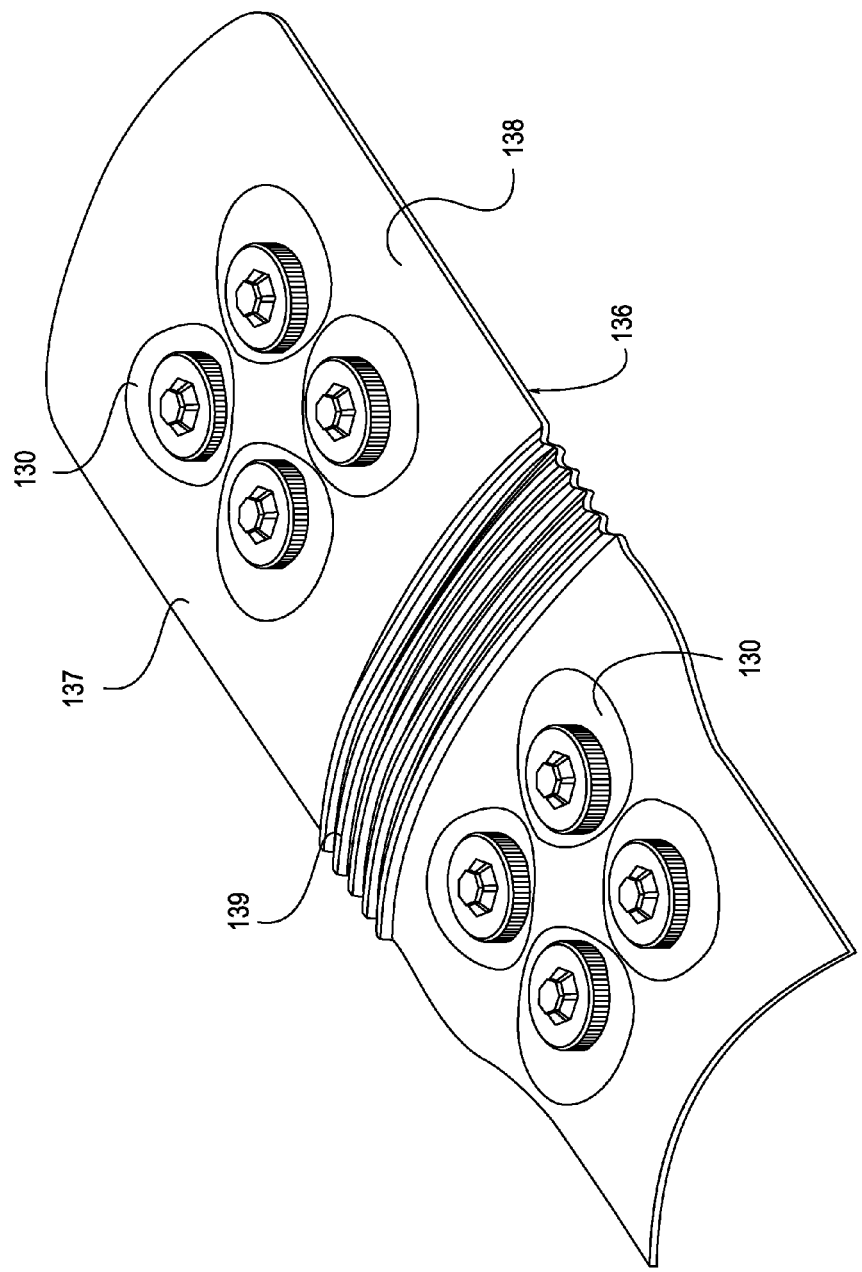

FIG. 6D illustrates a number of spline gears 130 forming part of a sterile drape or surgical barrier 137, which includes a surgical side 138 and a working side 136. The surgical barrier 137 can include any number of flexible spline gears 130 (where such spline gears 130 can be formed from or in the barrier 137). Alternatively, in additional variations, the spline gears 130 could be assembled into the surgical barrier 137. In certain variations, the surgical barrier 137 can be made from a different material than the spline gear 130 or can have different properties (e.g., stiff, absorbent, etc.). However, to maintain the benefits of the tool/driver module described above, the surgical barrier 137 as well as the spline gears 130 must be robust enough to withstand repeated placement and removal of the drive mechanism onto the spline gears 130 without losing or compromising sterility of the surgical field. In addition, the surgical barrier 137 can include any number of features to accommodate relative motion between adjacent groups of spline gears 130 (and ultimately the drive mechanism that are to be attached thereto). For example, the surgical barrier can include an area of increased flexure 139 to accommodate relative movement or rotation of the adjacent groups of spine gears 130 and drive mechanisms. The area of increased flexure 139 can include an accordion or corrugated section of the barrier 137.

FIGS. 7A through 7D illustrate variations of wave generators 116 for use with the motors 112 of the driver system 110 discussed above. Typically, the wave generator 116 the wave generator 116 can be directly driven by a motor 112. Alternatively it could be driven by any rotary axis motion, including a non-direct means including any configuration of gears, pulleys, etc. However, placement of motors underneath the drive mechanism 104 and in engagement with the wave generator 116 allows the motor to float with the tool/driver module 100 to achieve the benefits discussed above.

Figure 7A:
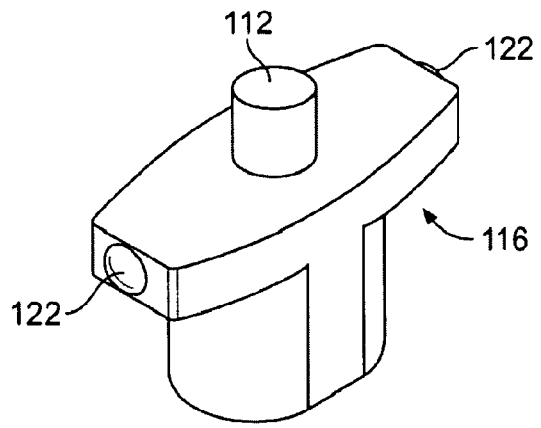
FIGS. 7A through 7D illustrate variations of wave generators for use with the harmonic motor assemblies.
Figure 7B:
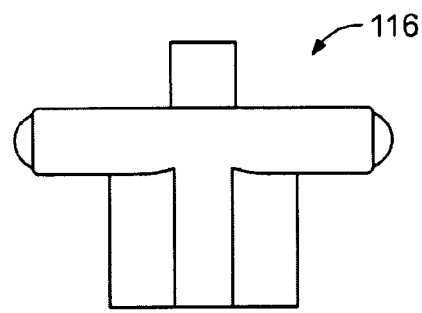

In any case, FIGS. 7A and 7B show respective perspective and side view of variation of a wave generator cam 116 having point contacts. In this example, the wave generator or wave generator cam 116 can be a sufficiently rigid material (e.g., a stainless steel member) with a spherical ball bearing 122 as a dual lobe on each side. The spherical ball-bearing configuration lends to point contacts on opposite ends of the wave generator cam 116 to engage a flexible spline. These point contacts reduce the force required to mate the flex spline/wave generator with the circular spline. However, because the point contacts also result in less contact (i.e. less teeth meshing) between the flexible spline and the circular spline gear, this configuration results in less drive force or a lower load rating.

Figure 7C:
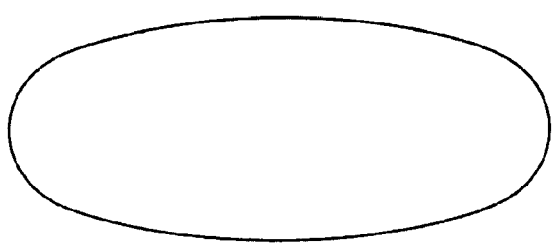
Figure 7D:
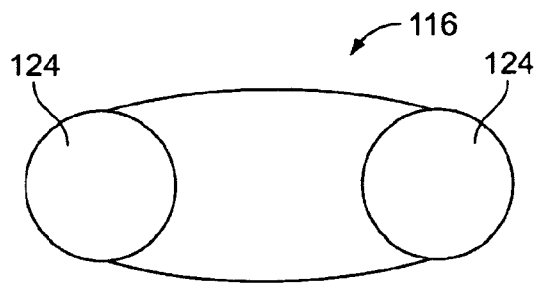

Accordingly, in additional variations, the tool/driver module 100 can incorporate a more traditional elliptical shape (as shown in FIG. 7C). This traditional shape results in a larger contact area between the wave generator and the flexible spline. The larger contact area allows for a higher drive force (i.e. a higher load rating). In yet an additional variation (as shown in FIG. 7D), a wave generator configuration can include rollers or roller bearings on either end. This configuration also increases the contact area between the wave generator and spline gear. While the increased contact area provides for higher load rating, it also requires a higher force to mate the flexible spline gear to the wave generator. Clearly, any number of variations of the shape and configuration of the wave generator cam are within the scope of this disclosure.

Figure 8A:
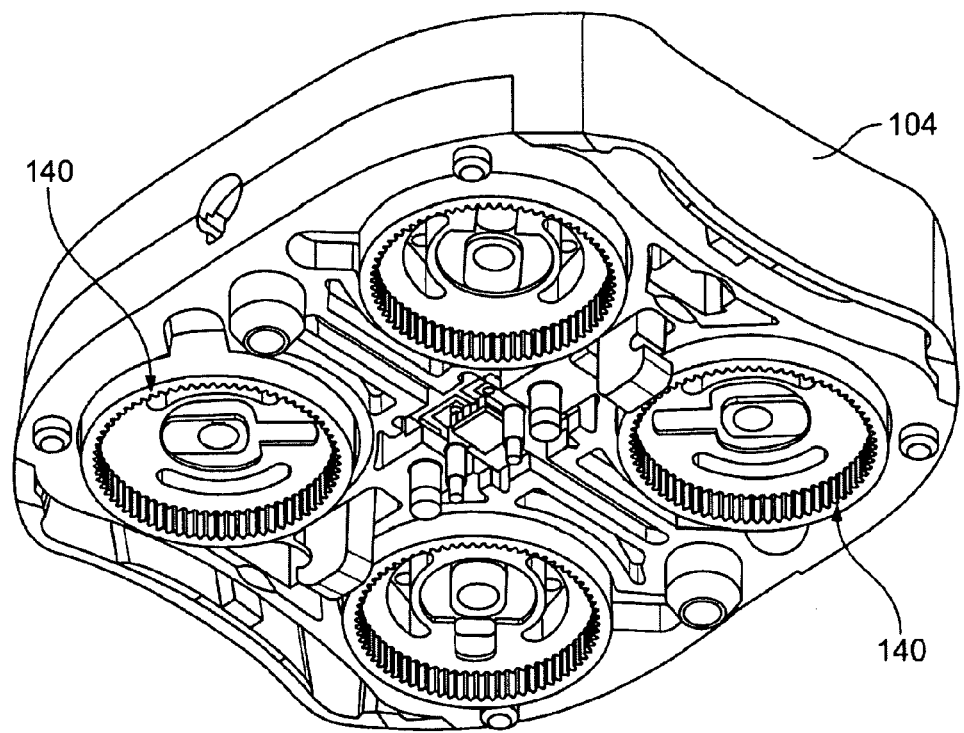
FIG. 8A illustrates a bottom perspective view of one example of a drive mechanism that houses a number of circular splines or spline gears.
Figure 8B:
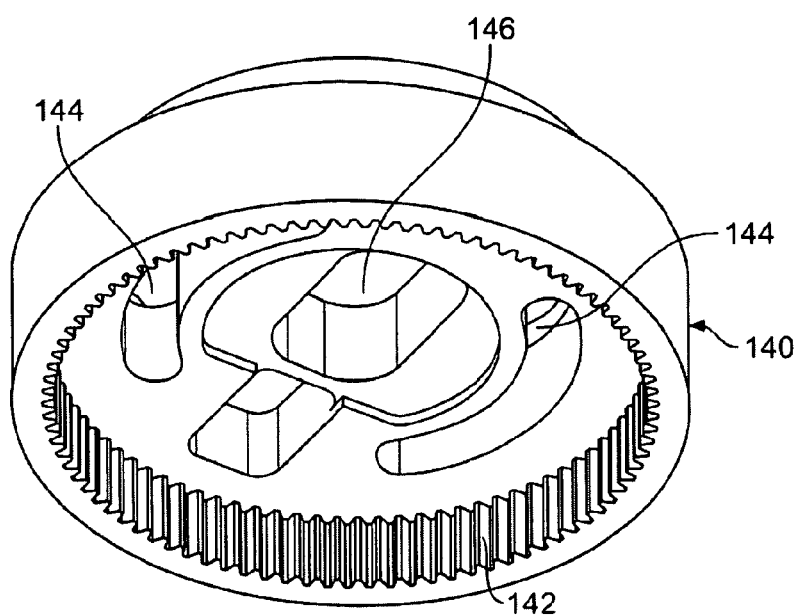
FIG. 8B illustrates an enlarged view of a circular spline gear.

FIG. 8A illustrates a bottom perspective view of a variation of a drive mechanism 104 that houses a number of circular splines or spline gears 140. The spine gears 140 are rotatable within the drive mechanism 104 to control a medical device (not shown) coupled to the drive mechanism 104. FIG. 8B illustrates an enlarged view of a circular spline gear 140 showing the gear teeth 142 as described above. As illustrated, the circular spline gear 140 can have any number of features 144, 146 that assist in retention of the circular spline gear 140 within the drive mechanism 104.

Figure 8D:
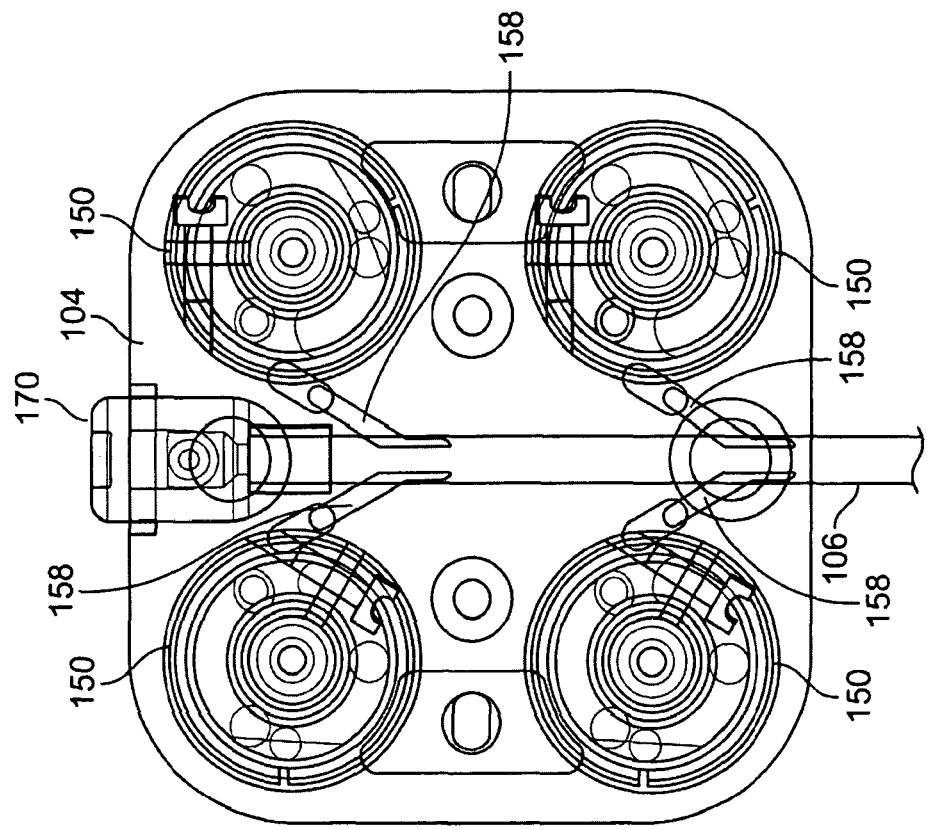
Figure 8C:
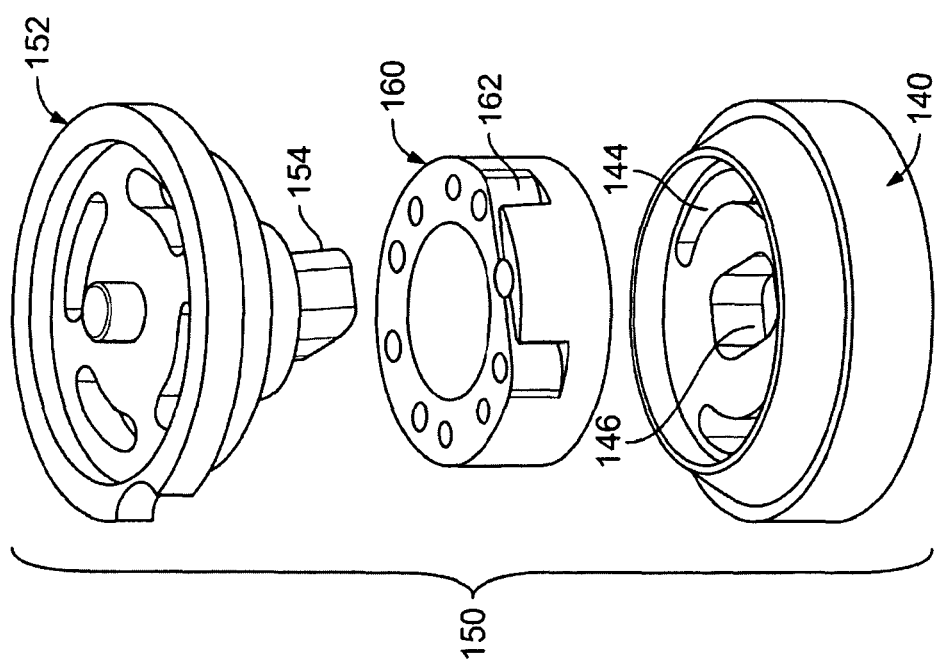

FIG. 8C illustrates an exploded view of the circular spline gear 140 as part of a drive pulley assembly 150 that fits within a drive mechanism 104. In this variation, the circular spline gear 140 functions as a lower drive pulley that receives a cable component 160. This variation of the drive pulley assembly 150 also includes an upper pulley 152 that includes an extension or protrusion 154 (in this example a rounded rectangular extension) that inserts directly into the circular spline gear 140 (lower drive pulley). In this manner, the circular spline gear 140 rotates the upper pulley 152 when driven by the flexible spline gear. The upper pulley 152, being coupled to the cable component 160 (e.g., using screws that pass through slots 144 in the upper pulley component 152) then rotates the cable component 160 to cause actuation steering, or other movement of a medical device coupled to the drive mechanism 104. The cable component 160 can include a cutout 162 formed to hold a crimp ball at the end of an actuation cable. Alternatively, the cable component 162 can drive the circular spline member to drive any rotary device including driving robotic end effectors, or even liner motion through a rack and pinion drive.

FIG. 8D shows one variation of a drive mechanism 104 with four drive pulley assemblies 150. The drive pulley assemblies 150 each include an actuation element (not shown) that is coupled to cable component 160. The actuation element couples to a medical device 106 via tracks 158 within the drive mechanism 104. The actuation elements (also known as control elements) can comprise solid wires made from materials such as stainless steel, which are sized for the anticipated loads and geometric parameters of the particular application. The actuation elements can be coated with materials such as a Teflon™ fluoropolymer resin from DuPont of Wilmington, Del. to reduce friction forces. Additional variations of such drive mechanisms that can be used with the devices, methods, and systems described in this disclosure are found in the commonly assigned applications referenced above.

Figure 9A:
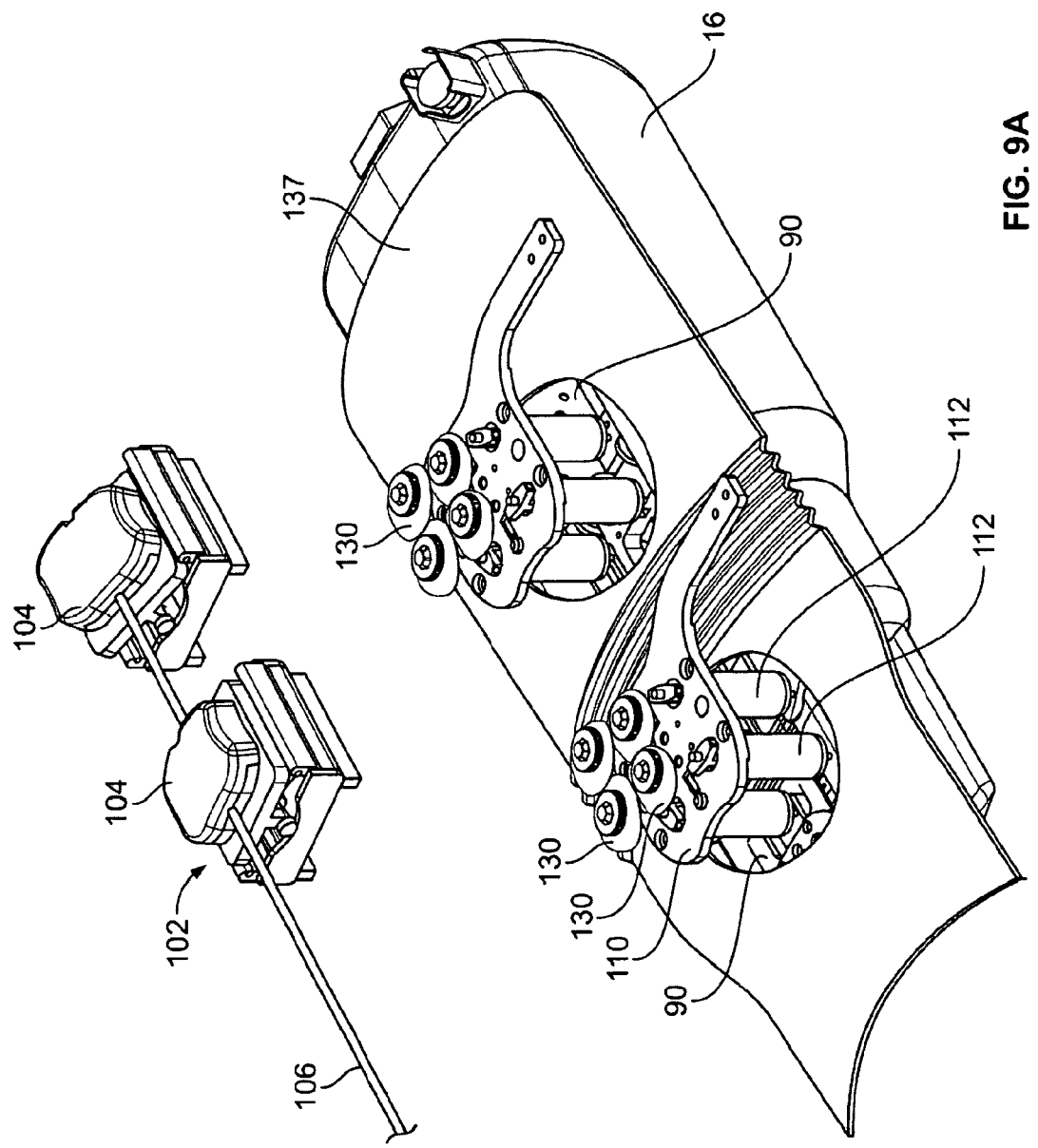
FIG. 9A illustrates a partial view of an RCM covered by a surgical barrier having a number of flexible spline cups.

FIG. 9A illustrates a partial view of an RCM 160 covered by a surgical barrier 137 having a number of flexible spline gears 130. As shown, the modular nature of the tool/driver modules permits the driver system 100 to be nested or seated in bays 90 of the RCM 16 and beneath the surgical barrier 137. The drive mechanism 104 of the medical tool 102 can be removably coupled over the spline gears 130 to engage the medical tool 102 with the RCM 16 and driver system 110. In the illustrated variation, the medical tool 102 includes two drive mechanism 104. In such a variation, one drive mechanism could couple to a sheath, while the other can couple to a guide or other medical device. However, any number of combinations or medical devices are within the scope of this disclosure.

Figure 9B:
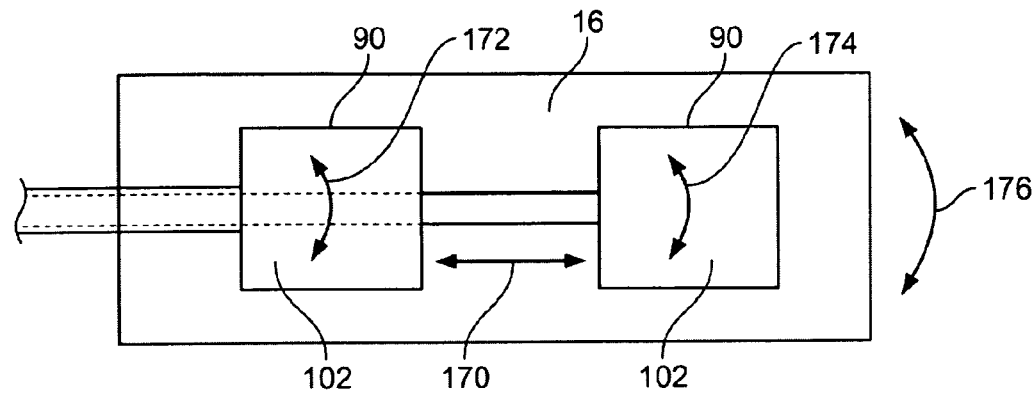
FIG. 9B illustrates a schematic illustration of an RCM having two bays each housing a medical tool.

FIG. 9B illustrates a schematic view of an RCM 16 having two bays 90 each housing a medical tool 102. As shown by arrow 170 the medical tools can move in an axial direction along the RCM 16 relative to one another. Alternatively, or in addition, the tools 102 can rotate relative to one another as indicated by arrows 172, and 174. As discussed above, placement of the motors directly beneath the medical tool 102 facilitates the ability to rotate the tools relative to each other. In addition, the entire RCM 16 can be rotated (as well as moved) with the tools 102.

Figure 10A:
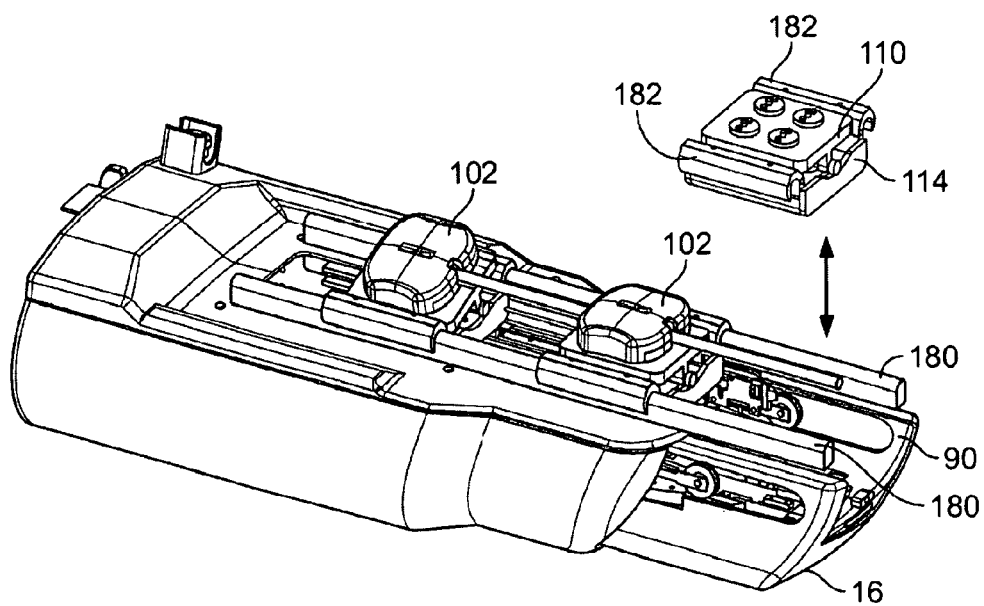
FIGS. 10A through 10F show variations of an RCM having a number of drive mechanism for medical tools where the drive mechanism move axially and rotationally relative to each other.
Figure 10B:
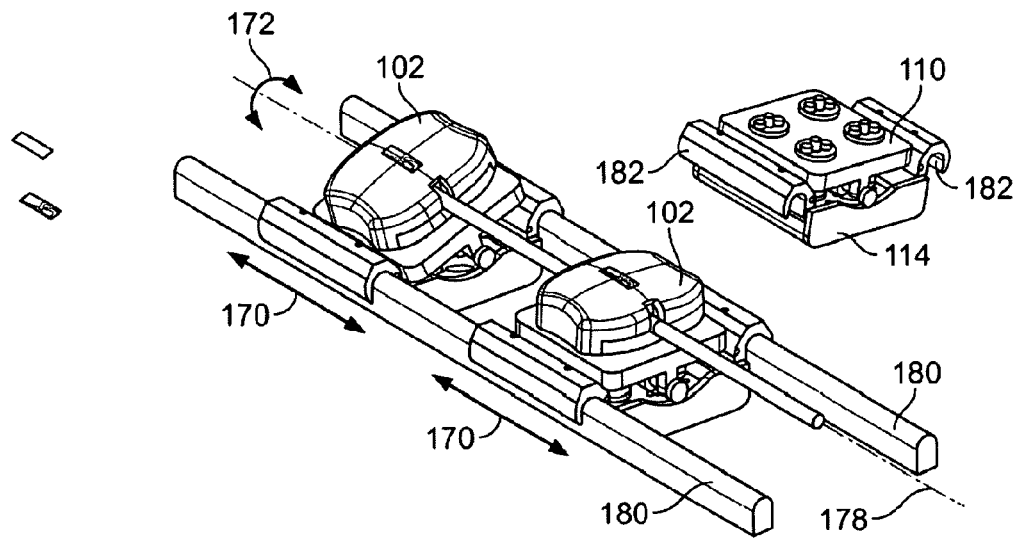

FIG. 10A shows a variation of an RCM 16 having a number of drive mechanism 110 that accept medical tools 102 where the drive mechanism 110 are able to move axially relative to each other. As shown, the drive mechanism 110 (either with or without a medical tool 102) can be coupled to the RCM 16 to allow for modular medical tools and drive mechanisms. In this variation, the RCM 16 includes one or more rails 180 allowing for guides or slides 182 on a base 114 of the drive mechanism 110 to couple thereto. The rail guides 182 allow for releasable coupling of the medical tool and/or drive mechanism 110. FIG. 10B illustrates the medical tool 102 and rails 180 of FIG. 10A without the RCM for sake of illustration. As shown, the base 114 of the drive mechanism 110 includes rail guides 182 that slide along the rails 180 allowing each medical device to move independently move as shown by element 170.

As discussed above, the use of small motors allows the entire drive mechanism 110 to be rotated relative to the RCM and other drive mechanism about an axis 172 (the axis can be offset from an axis of the RCM). The ability to independently rotate the various medical tools 102 relative to one another permits improved steering, positioning, or actuation of any number of medical devices. The axial movement of each base 114 can be controlled using a screw-drive type configuration. Alternatively, the rail guides 182 and rails 180 can function as linear drive motors where the rail functions as a stator 180 that drives the rail guides 182.

Figure 10C:
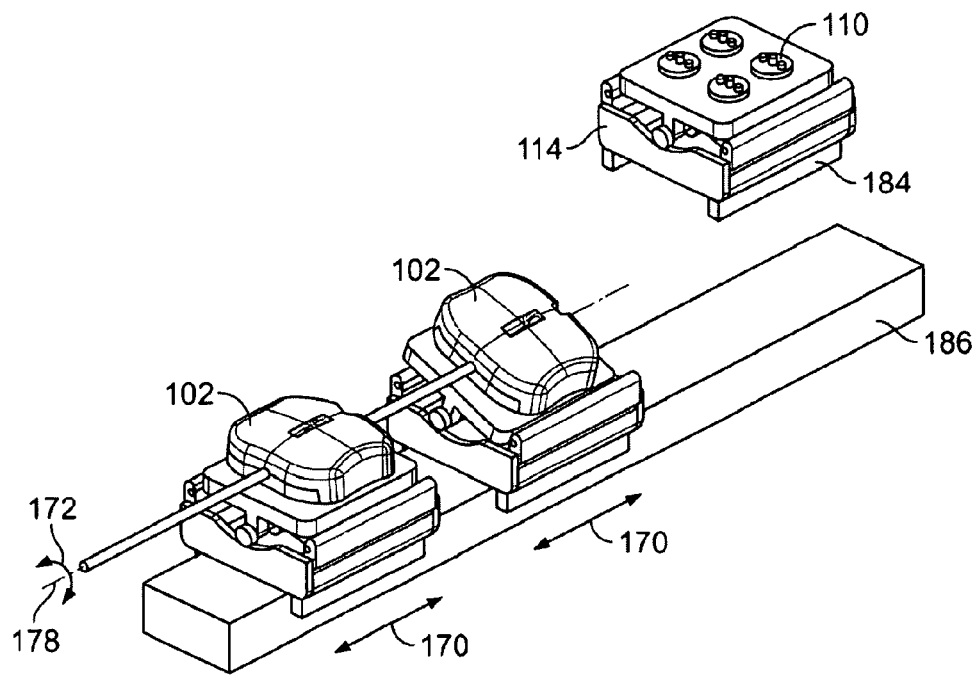

FIG. 10C illustrates another variation of a system for use with an RCM where the medical tools 140 are axially and rotationally positionable relative to each other. In this variation, the RCM (not pictured) is configured to couple to the base 114 in order to provide a linear drive motor system to position the medical tools 102. Linear drives typically include a stationary platen or stator (similar to a stator in a rotational motor) and a slider or forcer (similar to a rotor in a rotational motor) that moves along the stator. In this variation, the stator 186 is affixed to the RCM (not shown) and the base 114 includes forcer components 184.

Thus, the drive mechanism 114 (being affixed to the base 184) is driven with an AC or DC current that is applied to the stator 186. The linear configurations discussed in reference to FIGS. 10B and 10C allow for non-contact operation with non-wearing parts. This allows for placement of a drape or barrier between the base 114 and rail 180 or stator 186. As discussed herein, this barrier permits maintaining a sterile field when replacing drive systems 114 on the RCM.

Figure 10D:
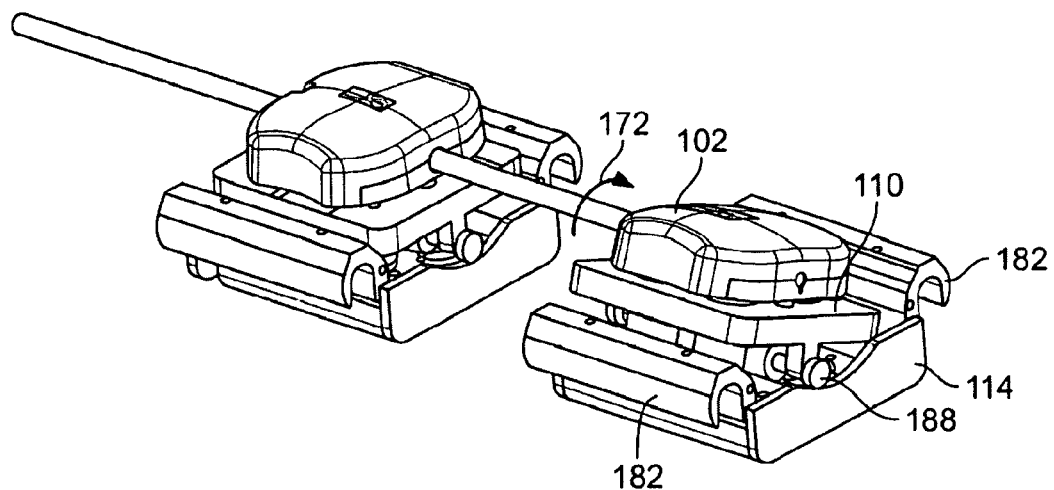
Figure 10E:
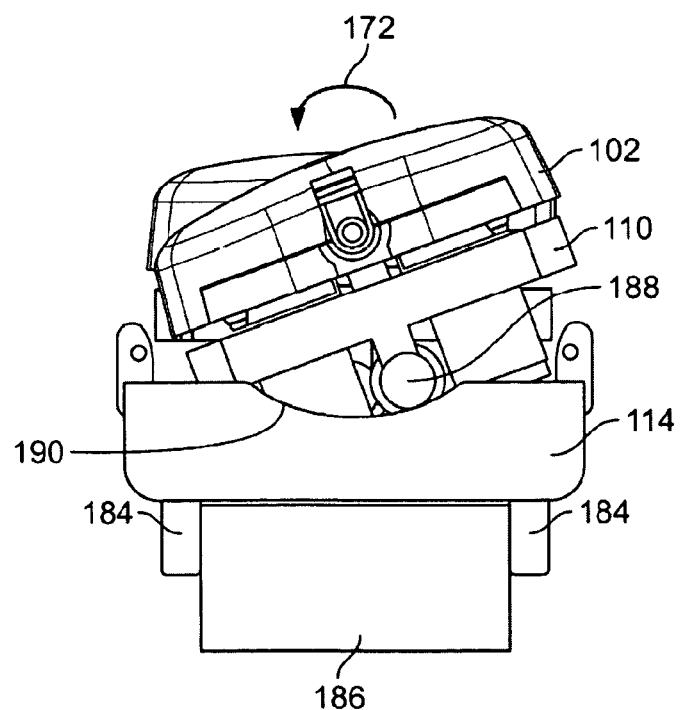
Figure 10F:
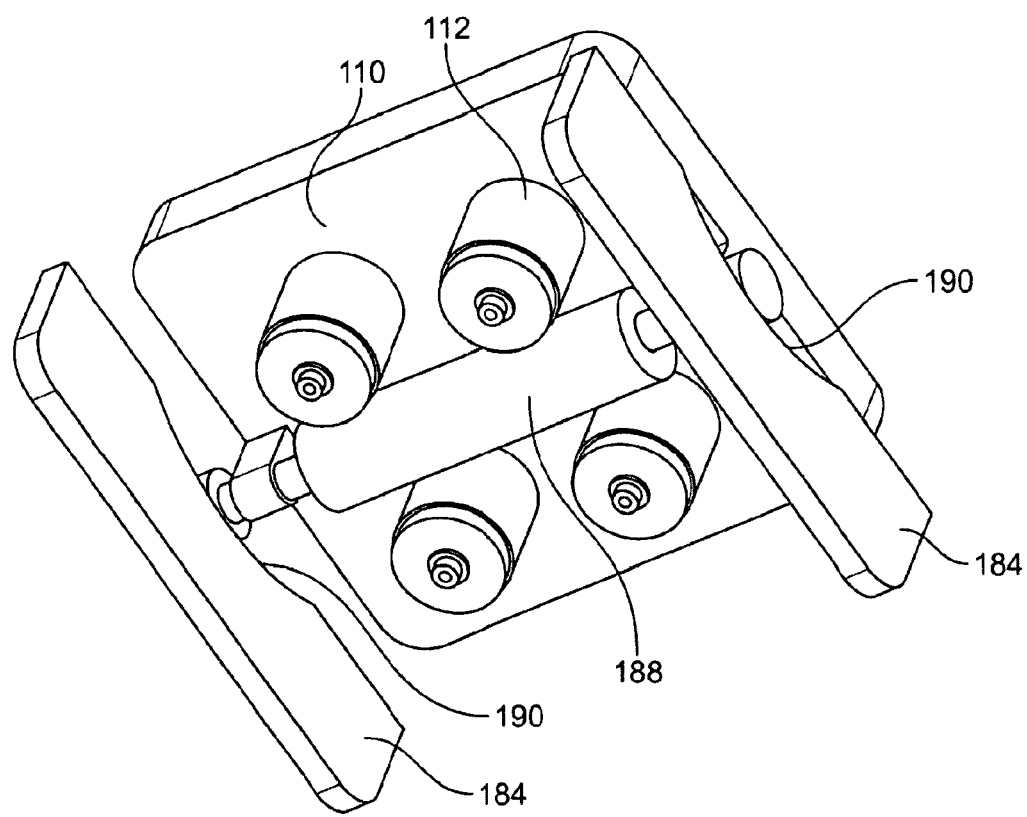

FIG. 10D illustrates another aspect of the drive mechanism 110 as having a positioning motor 188. In this variation, the positioning motor 188 engages the base 114 to rotate the drive mechanism 110 and medical tool 102 about an axis as shown by arrows 172. The interface between the positioning motor 188 and base 114 can be any commonly used interface (pinion gear, frictional interface, etc.) FIG. 10E illustrates a rear view of the assembly of FIG. 10D. As shown, the positioning motor 188 engages a concave track 190 in the base 114 to rotate the medical tool 102 about an axis. FIG. 10F illustrates a partial view from a bottom perspective of a drive mechanism 110 having a positioning motor 188 coupled to two concave tracks 190 in a base 114. The rotation of the base and medical tool can occur about an axis of the RCM or can occur about an axis that is offset from the axis of the RCM. For example, the depths and/or length concave track 190 can vary to modify the rotation of the drive mechanism 110 and medical tool 102.

Figure 11A:
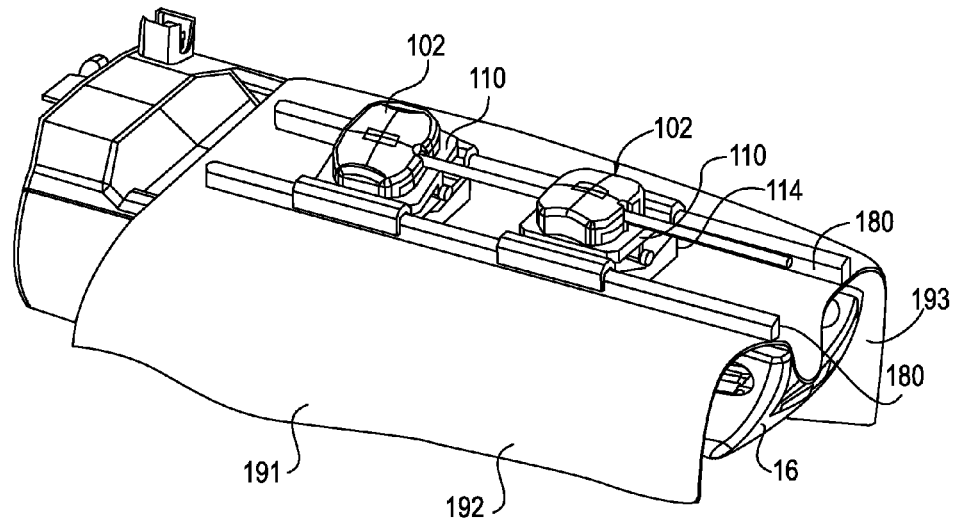
FIGS. 11A and 11B show an additional variation of the system including a drape that provides a sterile barrier between a component of an RCM and a drive system to preserve sterility when substituting a drive system on the RCM.
Figure 11B:
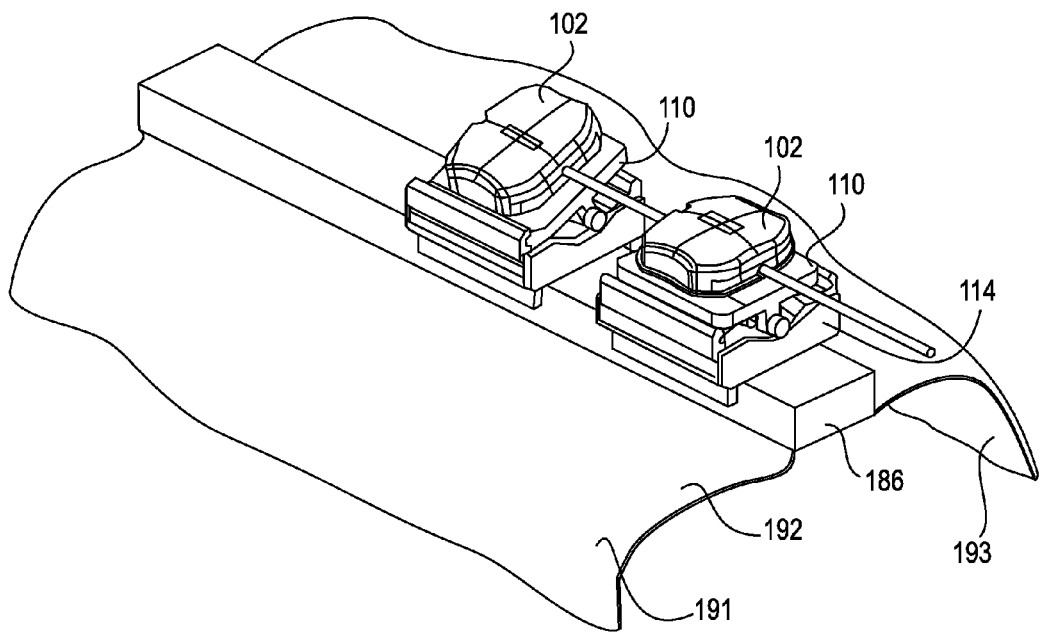

FIGS. 11A and 11B show an additional variation of the system described herein. In this variation, the rail 180 or stator 186 can include a drape 192 to provide a sterile barrier between the RCM 16 and the surgical field. Accordingly, the medical tool 102 and drive mechanism 110 along with the base 114 can be replaced during a surgical procedure while maintaining sterility when coupled to the RCM 16. As shown, the surgical barrier 192 can include a drape portion that encases the RCM 16 and includes a surgical side 191 and a working side 193. In additional variations, the surgical barrier 192 can be a fitted material that fits over the rail 180 or stator 186. In such a case the surgical barrier comprises a material (such as PTFE) that does not interfere with the interaction between the base 114, rail 180, rail guide 182, stator 186, and/or forcer component 184.

Figure 11C:
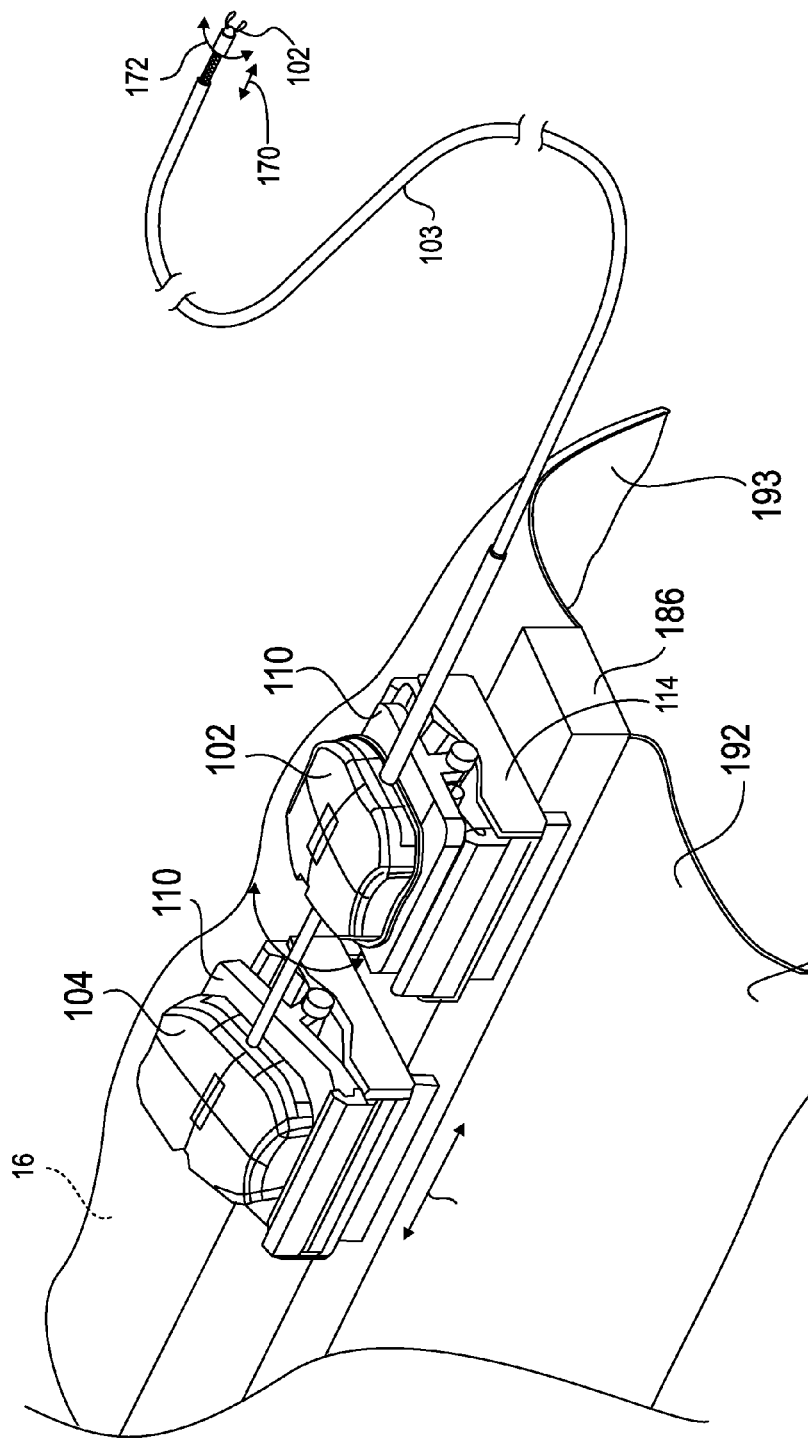
FIG. 11C illustrates an example of a pair of splayers or drive systems each able to rotate and axially translate relative to one another as well as an RCM where the first splayer controls a medical tool extending through a catheter coupled to a second splayer.

FIG. 11C illustrates a variation of the system shown in FIG. 11B (though the concept is applicable to any system described herein) where a pair of splayers or drive mechanism 104 each able to rotate and axially translate relative to one another as well as an RCM 16 (in this case the RCM is underneath a drape 192) where the first mechanism 104 controls a medical tool 102 extending through a catheter 103 coupled to a second mechanism 104. In this variation, the distal portion of the catheter 103 is shown curved ("S" shaped; i.e., a flexible distal portion). Typically, the distal portion of the catheter 103 extends within the anatomy of a patient. The second drive mechanism 104 coupled to the catheter 103 navigates the catheter 103 to the desired site. The first drive mechanism 104 controls a medical tool or device 102 that can exit from the distal end of the catheter 103 and can access the intended target site. The first drive mechanism 104 can actuate or control the medical device 102 interpedently of the catheter 103. For example, the first drive mechanism 104 and drive system 110 can rotate or translate the medical tool 102 as shown by arrows 170 (representing axial translation relative to the catheter and/or RCM) and 172 (representing rotational movement relative to the catheter and/or RCM).

Figure 12A:
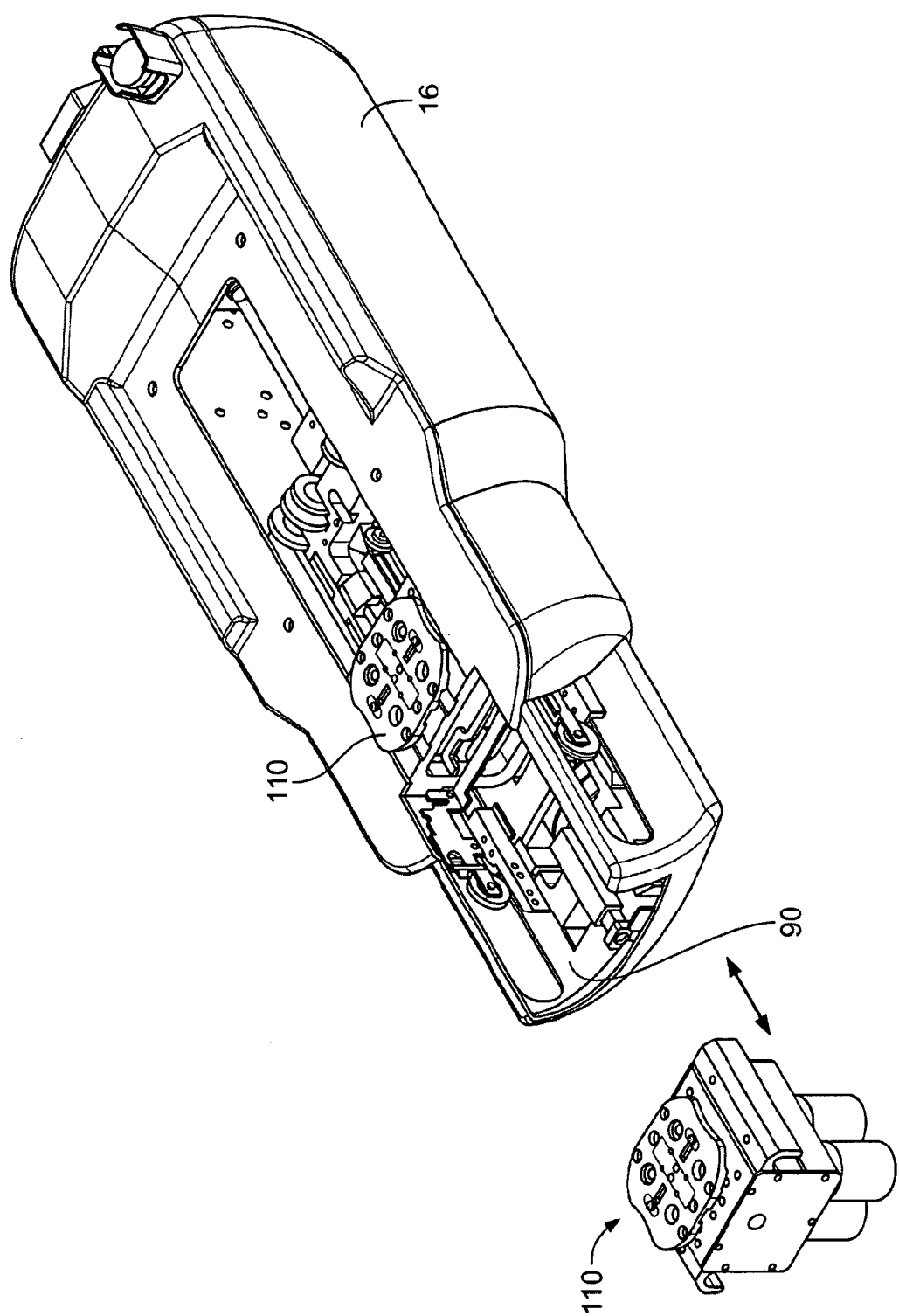
FIGS. 12A through 12C illustrate various configurations allowed by the modular nature of the present system.
Figure 12B:
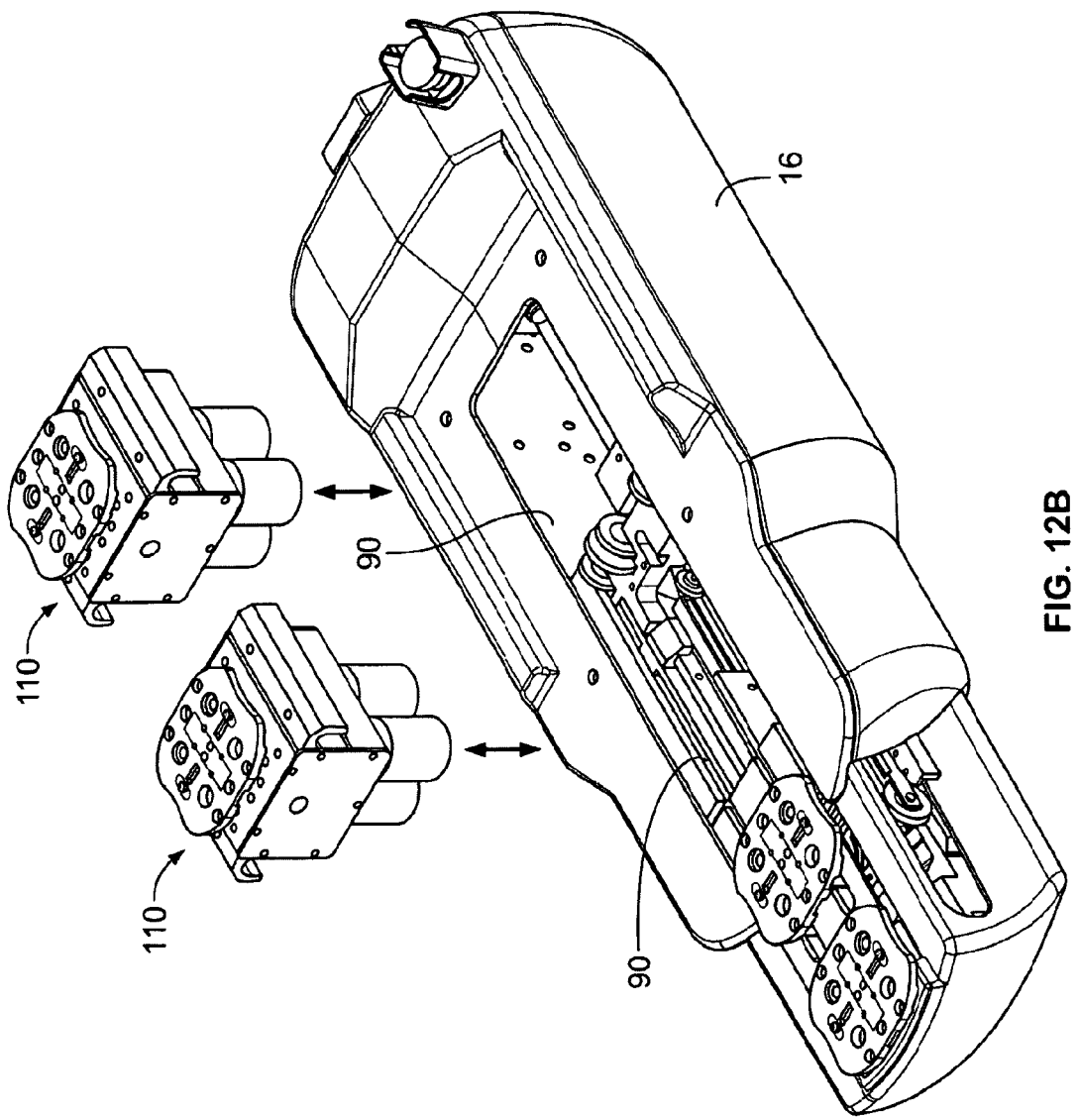
Figure 12C:
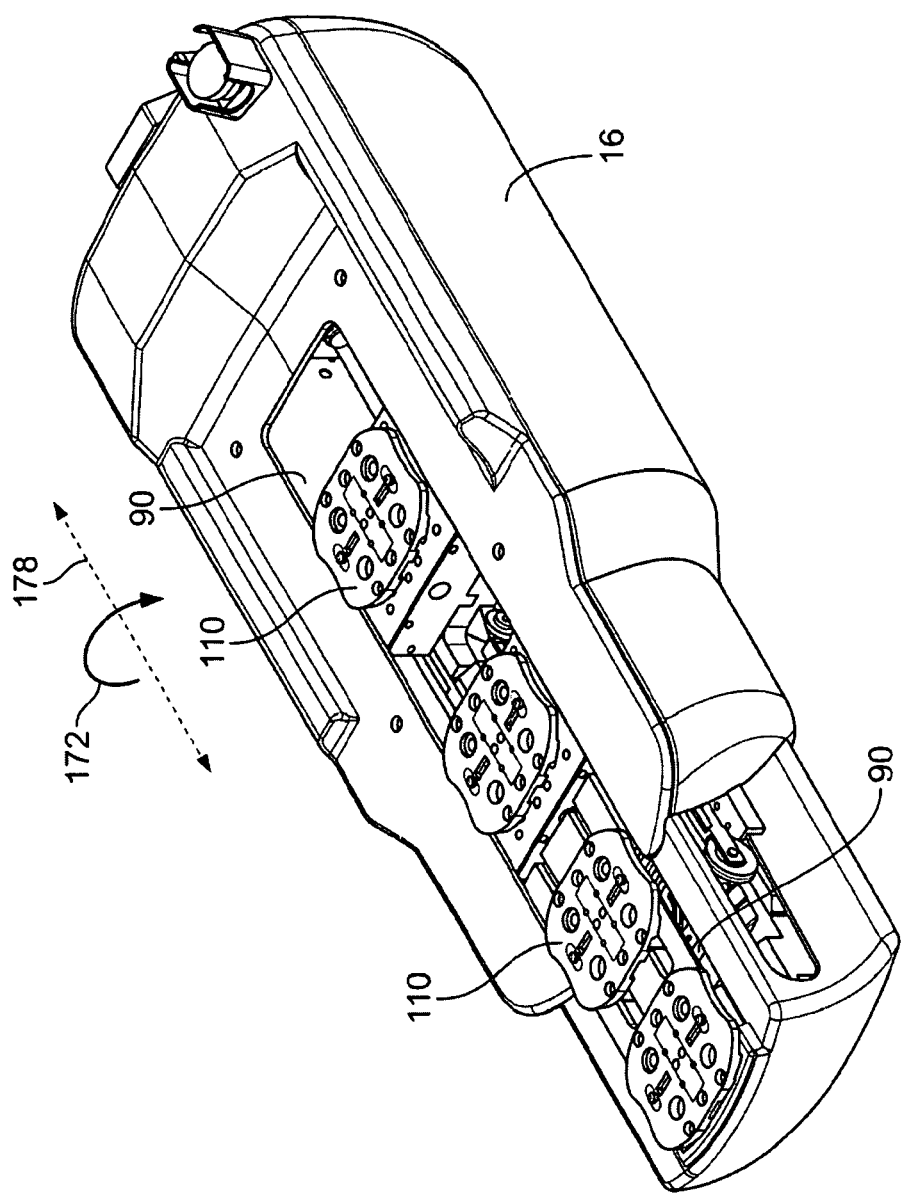

FIGS. 12A through 12C illustrate various configurations allowed by the modular nature of the present system. The RCM's 16 ability to accept modular drive mechanism 110 allows the user to add or subtract robotic capability by simply installing or removing drive mechanisms 110 modules. The modules are designed to operate like a cartridge, meaning that they can easily be attached and detached by the operator. The modules can have "plug-n-play" capability that allow quick installation to the base RCM 16 where the system recognize the module automatically. Different robotic tools and catheters may require the varying modules, each having different functions and interfaces, such as linear and rotational displacement features. As shown in FIGS. 12A and 12B, the modules can be loaded from the top, bottom, sides, front, or back of the RCM. The modules 110 simply dock into the bays 90 the RCM 16. Another benefit offered by the drive systems described herein is that each independent drive mechanism 110 can translate along a common axis 178 of the RCM 16 (typically the axis that runs along a length of the RCM 16.) The modular drive systems 110 can also independently rotate about the same common axis as shown by arrow 172 in order to provide additional degrees of freedom to the surgical tool or catheter that is coupled to the drive system 110. As illustrated the modular design of the RCM 16 permits leaving some bays empty.

Figure 13A:
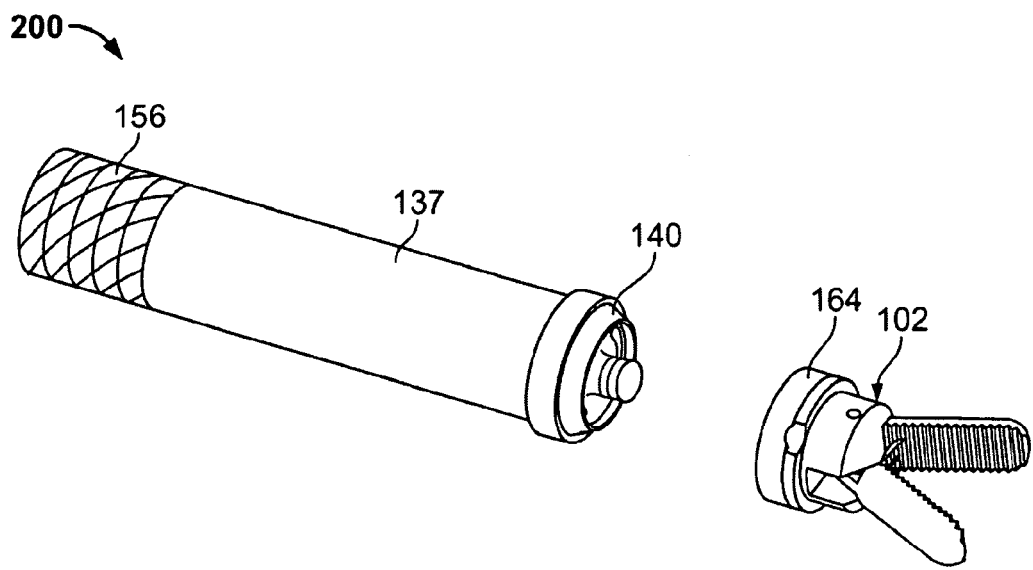
FIGS. 13A through 13C illustrate another variation of a portable device using a flexible spline gear.
Figure 13C:
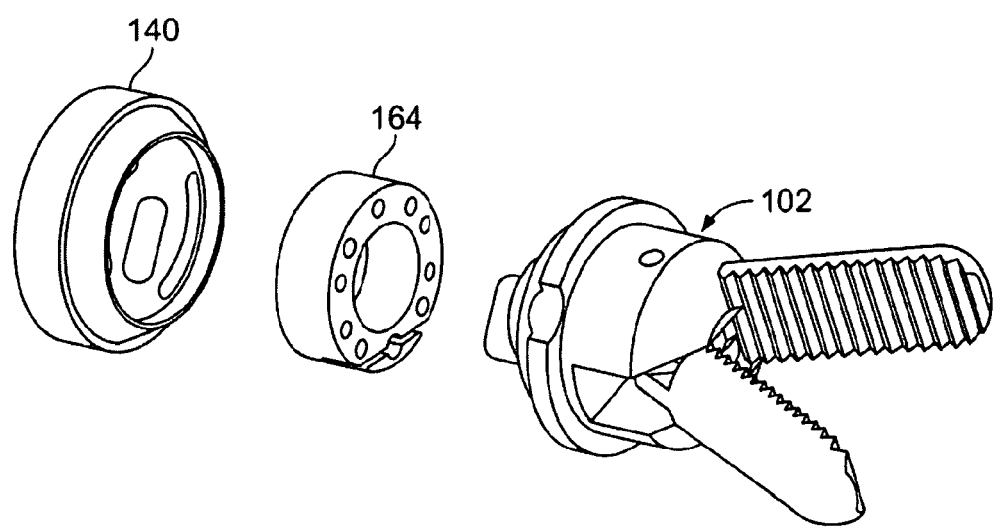
Figure 13B:
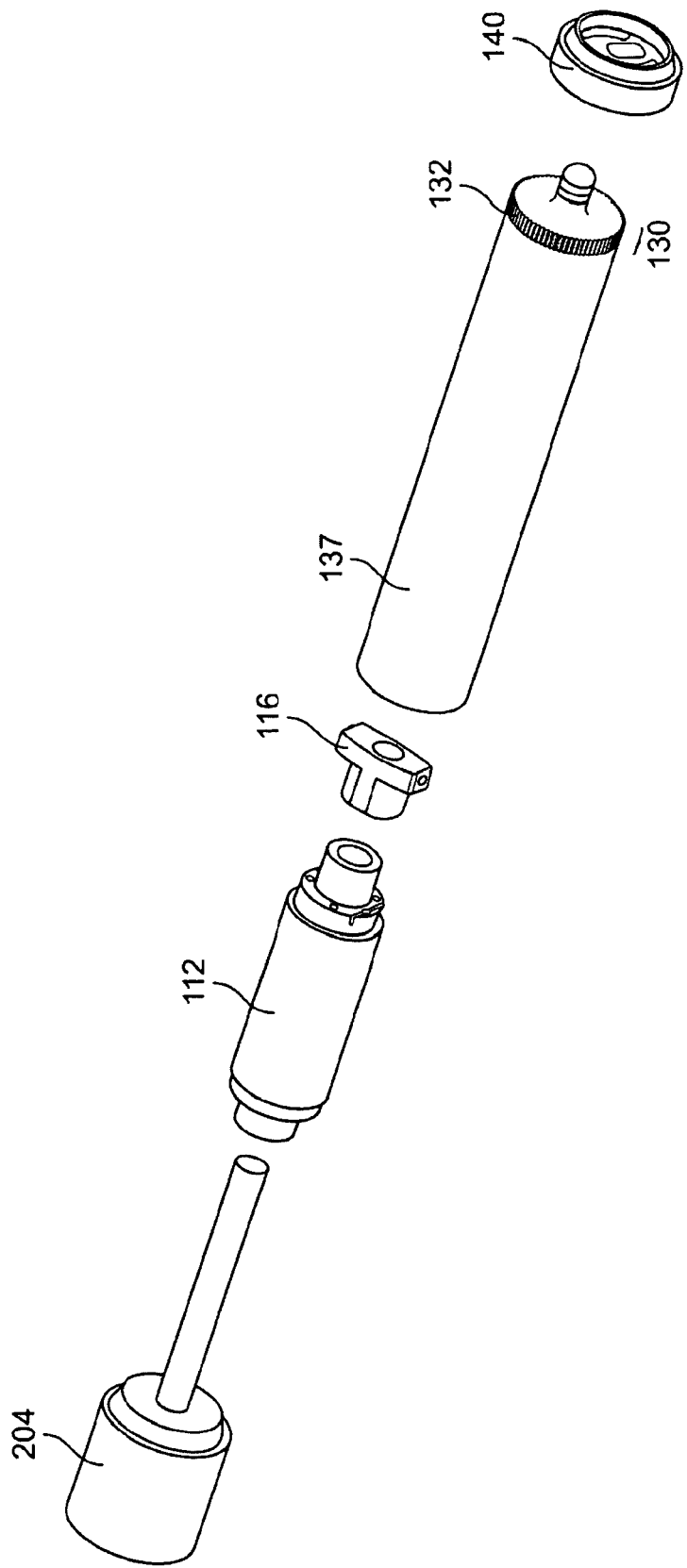

FIGS. 13A through 13C illustrate another variation of a device according to the present disclosure. In this variation, the device 200 comprises a portable or other tool that does not require robotic insert or actuation. In other words, the modular device 200 can be standalone or one that is attached to another structure (e.g., a bed, frame, etc.) and then coupled (via wireless or via a cable) to a control system. Although the present example shows a medical tool 102 comprising a grasper, any number of medical tools can be incorporated with the design (e.g., rotary drill, deburring device, cutters, shavers, etc.) Commonly assigned U.S. provisional application No. 60/902,144 discloses a number of additional medical devices or end effectors that can be implemented into the present design.

FIG. 13A shows the medical tool 102 coupled to a tool component 164 (as shown in FIG. 13C) that mates with a circular spline gear 140. In this variation, the gear 140 mates with a flexible spline 130 (but not shown in FIG. 13A) that engages the circular gear 140. The remainder of the flexible spline 130 comprises a surgical barrier 137, which in this variation comprises a pouch or an encasement that provides a sterile barrier to the motor assembly located therein. As shown, the barrier 137 can include a handle portion 156 or other section that allows manipulation or fixation of the tool 200.

FIG. 13B illustrates an exploded view of the motor unit 112 wave generating cam 116, surgical barrier 137, and circular spline gear 140. As shown, the flexible spline gear 130 is located at an end of the barrier 137 and includes a number of spline teeth 132 that engage a number of gear teeth located within the circular gear 140. FIG. 13B also shows use of an actuator motor 204. If more than one degree of actuated motion is desired, a hollow shaft motor 112 can be used. The hollow shaft motor 112 in conjunction with a lumen through the center of the wave generating cam 116 gives the ability to send a plurality of actuators through the center of the drive assembly. The flex spline gear 130 could be designed to allow for linear, rotary, or ballooning motion, or incorporate a second smaller diameter flex spline while still maintaining the sterile barrier. So while the original harmonic drive motor 112 actuates one motion (articulation of a catheter, or roll of the tool, etc.), the secondary actuator 204 could be used for any number of motions. For example the medical device 102 can be rotated about the tools 200 longitudinal axis, where the rotational motion is driven by the harmonic drive motor 112, wave generating cam 116, flexible spline gear 130 and circular spline gear 140. The secondary actuator 204 can drive the gripper 102 as shown. Alternatively, the secondary actuator 204 could drive any other type of motion depending upon the application.

As illustrated, the tool 200 permits driving a medical device 102 using a single motor. Since the motor is difficult or impractical to sterilize, the surgical barrier surrounds the entire motor assembly. Thus the entire assembly 200 is sterile. The assembly could be mounted on a small set-up joint (as disclosed in the above referenced commonly assigned patents and applications). In another variation, the device 200 can be sized appropriately so that it is insertable into a patient.

Although the methods and devices disclosed herein may be particularly useful in medical applications, one of ordinary skill in the art having the benefit of this disclosure would appreciate that such methods and devices may also be applicable generally in other robotic applications. As used in this specification and the appended claims, the singular forms "a," "an" and "the" include plural referents unless the context clearly dictates otherwise. Thus, for example, the term "a member" is intended to mean a single member or a combination of members, "a fluid" is intended to mean one or more fluids, or a mixture thereof. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above.

We claim:

1. A surgical barrier for use with a medical positioning system having a medical tool, where the medical positioning system includes at least a driver mechanism to affect a position of the medical tool, the surgical barrier comprising:
    a sterilizable drape portion, comprising a surgical side and a working side, wherein the working side is adapted to contact a portion of the medical positioning system, while a sterile surgical field is preserved on the surgical side;
    at least one flexible cup in the drape portion, wherein a working side of the at least one flexible cup is configured to couple to a portion of the driver mechanism, wherein at least a portion of a surgical side of the at least one flexible cup couples to the medical tool, and wherein the at least one flexible cup is configured to deform and transfer motion from the driver mechanism of the medical positioning system to the medical tool; and
    a flexure area in the sterilizable drape portion, wherein the flexure area accommodates movement or rotation of the at least one flexible cup and the driver mechanism.

2. The surgical barrier of claim 1, wherein the at least one flexible cup comprises a plurality of spline teeth.

3. The surgical barrier of claim 2, wherein the driver mechanism of the medical tool comprises a plurality of gear teeth on the driver mechanism, and the at least one flexible cup is configured to deform in response to a driver portion, causing the spline teeth to engage the gear teeth.

4. The surgical barrier of claim 3, wherein a number of spline teeth is not equal to a number of gear teeth.

5. The surgical barrier of claim 1, wherein the at least one flexible cup comprises a first plurality of cups.

6. The surgical barrier of claim 5, wherein the at least one flexible cup additionally comprises at least a second plurality of cups spaced along the drape portion apart from the first plurality of cups.

7. The surgical barrier of claim 1, wherein the sterilizable drape portion has a different flexibility than a flexibility of the at least one flexible cup.

8. The surgical barrier of claim 1, wherein the drape portion is sized to enclose the medical positioning system.

9. The surgical barrier of claim 1, wherein the at least one flexible cup is configured to deform and transfer rotary motion from the driver mechanism of the medical positioning system to the medical tool.

10. The surgical barrier of claim 1, wherein the at least one flexible cup is configured to deform and transfer linear motion from the driver mechanism of the medical positioning system to the medical tool.

11. A surgical barrier for use with a medical positioning system having a medical tool, where the medical positioning system includes at least a driver mechanism to affect a position of the medical tool, the surgical barrier comprising:
    a sterilizable drape portion, comprising a surgical side and a working side, wherein the working side is adapted to contact a portion of the medical positioning system, while a sterile surgical field is preserved on the surgical side;
    at least one flexible encasement in the drape portion, wherein a working side of the at least one flexible encasement is coupled to the driver mechanism, wherein at least a portion of a surgical side of the at least one flexible encasement is coupled to the medical tool, and wherein the at least one flexible encasement is configured to deform and transfer motion from the driver mechanism of the medical positioning system to the medical tool; and a flexure area in the sterilizable drape portion, wherein the flexure area accommodates movement or rotation of the at least one flexible encasement and the driver mechanism.

12. The surgical barrier of claim 11, wherein the at least one flexible encasement comprises a cup.

13. The surgical barrier of claim 11, wherein the at least one flexible encasement comprises a plurality of spline teeth.

14. The surgical barrier of claim 11, wherein the driver mechanism of the medical tool comprises a plurality of gear teeth on the driver mechanism, and the at least one flexible encasement is configured to deform in response to a driver portion, causing the spline teeth to engage the gear teeth.

15. The surgical barrier of claim 11, wherein the sterilizable drape portion has a different flexibility than a flexibility of the at least one flexible encasement.

16. The surgical barrier of claim 11, wherein the at least one flexible encasement is configured to deform and transfer rotary motion from the driver mechanism of the medical positioning system to the medical tool.

* * * * *